US012708189B2

(12) United States Patent
Ikeyama et al.

(10) Patent No.: US 12,708,189 B2
(45) Date of Patent: Aug. 18, 2026

(54) SHEET-PROVIDING METHOD AND SHEET-PROVIDING SYSTEM

(71) Applicant: Kao Corporation, Tokyo (JP)

(72) Inventors: Suguru Ikeyama, Ichikai-machi (JP); Naomi Amari, Ichikai-machi (JP); Shunetsu Yonaiyama, Utsunomiya (JP); Hiroya Suzuki, Utsunomiya (JP); Takehiko Tojo, Utsunomiya (JP); Hideo Kobayashi, Koto-ku (JP)

(73) Assignee: Kao Corporation, Tokyo (JP)

( * ) Notice: Subject to any disclaimer, the term of this patent is extended or adjusted under 35 U.S.C. 154(b) by 1079 days.

(21) Appl. No.: 17/790,844

(22) PCT Filed: Dec. 24, 2020

(86) PCT No.: PCT/JP2020/048586
§ 371 (c)(1),
(2) Date: Jul. 5, 2022

(87) PCT Pub. No.: WO2021/140945
PCT Pub. Date: Jul. 15, 2021

(65) Prior Publication Data

US 2023/0041172 A1 Feb. 9, 2023

(30) Foreign Application Priority Data

Jan. 6, 2020 (JP) ................................ 2020-000116

(51) Int. Cl.
*A45D 44/00* (2006.01)
*A45D 44/22* (2006.01)
*A61K 8/02* (2006.01)

(52) U.S. Cl.
CPC ......... *A45D 44/002* (2013.01); *A45D 44/005* (2013.01); *A61K 8/02* (2013.01); *A45D 2044/007* (2013.01); *A45D 44/22* (2013.01)

(58) Field of Classification Search
CPC .... G06Q 30/0621; G06Q 50/04; G06Q 30/01; G16Y 20/40; G16Y 10/60; A45D 44/005;
(Continued)

(56) References Cited

U.S. PATENT DOCUMENTS 8,597,667 B2 * 12/2013 Mou .................... A45D 44/005 424/444
2002/0194021 A1 12/2002 Matsumoto et al.
(Continued)

FOREIGN PATENT DOCUMENTS

CN 201558223 U 8/2010
CN 104203043 A 12/2014
(Continued)

OTHER PUBLICATIONS

International Search report issued Mar. 9, 2021 in PCT/JP2020/048586, filed on Dec. 24, 2020, (3 pages).

*Primary Examiner* — An H Do
(74) *Attorney, Agent, or Firm* — Oblon, McClelland, Maier & Neustadt, L.L.P.

(57) ABSTRACT

A sheet providing method provides a sheet that is used by being applied to a body surface of an individual user. The method involves determining a shape and dimensions of a sheet for each individual user U based on body surface information of the individual user; and forming the sheet by controlling a discharge nozzle that discharges a raw material of the sheet based on information regarding the shape and the dimensions of the sheet. Also, a sheet providing system having a sheet specification determining unit that determines a shape and dimensions of a sheet for each individual user based on body surface information of the individual user; and a sheet forming unit that forms the sheet by controlling
(Continued)

a discharge nozzle that discharges a raw material of the sheet based on information regarding the shape and the dimensions of the sheet.

16 Claims, 11 Drawing Sheets

(58) Field of Classification Search
CPC ............ A45D 44/002; A45D 2044/007; A45D 44/22; G06T 19/20; G06T 2219/2021; A61K 8/02
See application file for complete search history.

(56) References Cited

U.S. PATENT DOCUMENTS

| | | | |
|---|---|---|---|
| 2009/0280150 | A1 | 11/2009 | Kamen et al. |
| 2010/0068247 | A1 | 3/2010 | Mou et al. |
| 2011/0123703 | A1 | 5/2011 | Mohammadi et al. |
| 2011/0300196 | A1 | 12/2011 | Mohammadi et al. |
| 2012/0325141 | A1 | 12/2012 | Mohammadi et al. |
| 2014/0146190 | A1 | 5/2014 | Mohammadi et al. |
| 2015/0059800 | A1 | 3/2015 | Shinoda et al. |
| 2015/0086945 | A1 | 3/2015 | Yamanashi et al. |
| 2016/0089535 | A1 | 3/2016 | Mohammadi et al. |
| 2016/0143420 | A1 | 5/2016 | Yamanashi et al. |
| 2016/0143421 | A1 | 5/2016 | Yamanashi et al. |
| 2016/0158123 | A1 | 6/2016 | Agarwal et al. |
| 2016/0316890 | A1 | 11/2016 | Samain et al. |
| 2018/0206616 | A1 | 7/2018 | Alary et al. |
| 2018/0276453 | A1 | 9/2018 | Takei |
| 2019/0098149 | A1 | 3/2019 | Shinoda |
| 2019/0192389 | A1 | 6/2019 | Shinoda |
| 2019/0200732 | A1 | 7/2019 | Shinoda et al. |
| 2020/0113314 | A1 | 4/2020 | Shinoda et al. |
| 2020/0215356 | A1 | 7/2020 | Onodera et al. |
| 2020/0250404 | A1 | 8/2020 | Shinoda et al. |

FOREIGN PATENT DOCUMENTS

| | | | |
|---|---|---|---|
| CN | 105407975 | A | 3/2016 |
| CN | 106998890 | A | 8/2017 |
| CN | 107374986 | A | 11/2017 |
| CN | 206675742 | U | 11/2017 |
| CN | 208756322 | U | 4/2019 |
| CN | 110139639 | A | 8/2019 |
| EP | 3 144 031 | A1 | 3/2017 |
| EP | 3 900 947 | A1 | 10/2021 |
| JP | 2012-502908 | A | 2/2012 |
| JP | 2013-28552 | A | 2/2013 |
| JP | 2014-152160 | A | 8/2014 |
| JP | 2015-43836 | A | 3/2015 |
| JP | 2017-500366 | A | 1/2017 |
| JP | 2019-115653 | A | 7/2018 |
| JP | 2019-49380 | A | 3/2019 |
| JP | 2019-73490 | A | 5/2019 |
| KR | 20-2009-0001277 | U | 2/2009 |
| KR | 10-2018-0102938 | A | 9/2018 |
| KR | 10-2019-0133420 | A | 12/2019 |
| WO | WO 2014/125407 | A1 | 8/2014 |
| WO | WO-2014/132594 | A1 | 9/2014 |
| WO | WO 2017/125975 | A1 | 7/2017 |
| WO | WO 2018/003421 | A1 | 1/2018 |
| WO | WO-2018/061486 | A1 | 4/2018 |
| WO | WO 2018/061595 | A1 | 4/2018 |
| WO | WO-2018/081596 | A1 | 4/2018 |
| WO | WO 2019/003649 | A1 | 1/2019 |
| WO | WO 2019/073626 | A1 | 4/2019 |

* cited by examiner (a)

(b)

SHEET-PROVIDING METHOD AND SHEET-PROVIDING SYSTEM

CROSS-REFERENCE TO RELATED APPLICATIONS

The present application is a 35 U.S.C. § 371 national stage application of International patent application PCT/JP2020/048586, filed Dec. 24, 2020, which is based on and claims the benefit of priority to Japanese Application No. 2020-000116, filed Jan. 6, 2020. The entire contents of these applications are incorporated herein by reference.

TECHNICAL FIELD

The present invention relates to a sheet providing method and a sheet providing system.

BACKGROUND ART

Cosmetic sheets that are applied to the skin to conceal spots and wrinkles are known. For example, Patent Document 1 discloses a serum impregnated cosmetic sheet that has a shape in plan view such as a circle or a crescent.

In the market of cosmetics such as cosmetic sheets, a standardized production technique is used to mass produce cosmetic products of the same specifications. In contrast, in recent years, a One-to-One production technique that meets the needs of individual customers based on preferences, attributes, and the like of the customers (users) has garnered attention. As an example of this technique, Patent Document 2 discloses a method of preparing and selling liquid cosmetic products, wherein a plurality of types of raw material solutions for cosmetic products that has different functions or different properties is loaded into containers at blending ratios desired by consumers, and then sold. The selling method is aimed to provide cosmetic products suited to a skin type, a texture, preferences, and the like of each individual user.

CITATION LIST

Patent Literature

Patent Literature 1: JP 2013-028552A

Patent Literature 2: US2002/194021A1

SUMMARY OF INVENTION

The present invention relates to a sheet providing method for providing a sheet that is used by being applied to a body surface of an individual user.

The sheet providing method comprises:

- a determining step of determining a shape and dimensions of a sheet for each individual user based on body surface information of the individual user; and
- a forming step of forming the sheet by controlling a discharge nozzle that discharges a raw material of the sheet based on information regarding the shape and the dimensions of the sheet.

With the sheet providing method of the present invention, since the sheet providing method includes the determining step and the forming step, a sheet having a shape and dimensions suited to an individual user can be provided to the individual user.

Also, the present invention relates to a sheet providing system that provides a sheet that is used by being applied to a body surface of an individual user.

The sheet providing system comprises:

- a sheet specification determining unit that determines a shape and dimensions of a sheet for each individual user based on body surface information of the individual user; and
- a sheet forming unit that forms the sheet by controlling a discharge nozzle that discharges a raw material of the sheet based on information regarding the shape and the dimensions of the sheet.

With the sheet providing system of the present invention, since the sheet providing system includes the sheet specification determining unit and the sheet forming unit, a sheet having a shape and dimensions suited to an individual user can be provided to the individual user.

DESCRIPTION OF EMBODIMENTS

The One-to-One production technique is more effective in improving customer satisfaction than standardized mass production techniques because it can reflect the wishes (needs) of users. In the case where the One-to-One production technique is used to provide a sheet that is used by being applied to the skin, it is desirable that the sheet is provided in a shape and a size appropriate for a body part to which the sheet is to be applied, or the size of the body part. However, the technique disclosed in Patent Literature 1 does not give consideration to the One-to-One production technique. The technique disclosed in Patent Literature 2 does not give consideration to providing the sheet in an appropriate shape and size.

Accordingly, the present invention relates to a sheet providing method and a sheet providing system, with which the problems encountered with the conventional techniques can be solved.

Hereinafter, the present invention will be described by way of a preferred embodiment thereof with reference to the drawings. In the specification of the present application, "sheet providing method" refers to a method of providing a sheet to a user who is a purchaser of the sheet by taking the One-to-One production technique described above into consideration. The sheet is used by being applied to a body surface such as skin. There is no particular limitation on body parts to which the sheet can be applied. Examples of the body parts include: a part of face such as a forehead, a nose, a lower eyelid, a cheek, and an ear; a part of hand such as a finger, a palm, the back of the hand; an upper arm; an elbow; a lower arm; a part of foot such as a toe and the sole of the foot; a thigh, the back of the body, chest, a shoulder, neck, head, hip, and the like. The sheet may be applied to a plurality of body parts that are adjacent to each other.

Figure 1:
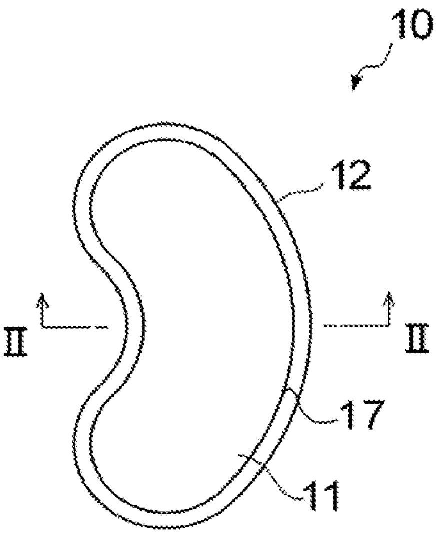
FIG. 1 is a plan view showing a sheet according to an embodiment of the present invention.

The sheet providing method according to the present invention is preferably used in various types of cosmetic methods that are not intended for surgery, treatment, and diagnosis methods performed on a human body. FIG. 1 shows a sheet according to an embodiment of the present invention. A sheet 10 according to the present embodiment is applied to a body surface of an individual user and thereby used to improve an outer appearance and a state of the body surface. For example, the sheet 10 can be used for cosmetic purposes such as whitening of skin to which the sheet 10 is applied, concealing spots on skin, concealing skin dullness and shadows on skin, concealing wrinkles on skin, blurring skin, protecting skin from ultraviolet rays, and moisturizing skin. Other than the above, the sheet 10 can also be used for various types of actions that are personally performed at home to protect skin, such as, for example, protecting various types of wounds including a scratch, a cut, a laceration, a stab wound, and the like, as well as preventing bedsores.

There is no particular limitation on the shape in plan view of the sheet 10 of the present embodiment, and the sheet 10 can have any shape in plan view according to the user needs. For example, the shape in plan view of the sheet 10 may be a geometric shape, such as a polygon such as a triangle, a quadrilateral, or a hexagon, or a circle or an ellipse. Also, the shape in plan view of the sheet may be a shape that has a profile including a plurality of curve portions of different curvatures as shown in FIG. 1, or a shape that has a profile including a linear portion(s) and a curve portion(s).

From the viewpoint of more appropriately applying the sheet 10 to a body part, it is preferable that the sheet 10 has a shape that corresponds to the body part to which the sheet 10 is to be applied. For example, in the case where the sheet 10 is to be applied to the lower eyelid, it is preferable that the profile of the sheet 10 includes a curve portion that is curved along the rim of the eye (see FIG. 1). For example, in the case where the sheet 10 is to be applied to an entire face, it is preferable that the sheet 10 has a profile that is substantially the same as that of the face, and also has opening portions at positions corresponding to the eyes, the nostrils, and the mouth.

The sheet 10 of the present embodiment comprises a base layer 12 and a sheet layer 11 that is to be applied to the skin. The sheet layer 11 of the present embodiment is made using a coating-formable polymer compound as a raw material, and is formed by discharging the raw material in a liquid state from a discharge nozzle, which will be described later. That is, the sheet layer 11 is formed by discharging the raw material in a liquid state onto one surface of the base layer 12. The sheet layer 11 is actually very thin, but is illustrated as being very thick in FIG. 2 for the sake of convenience of description.

Figure 2:
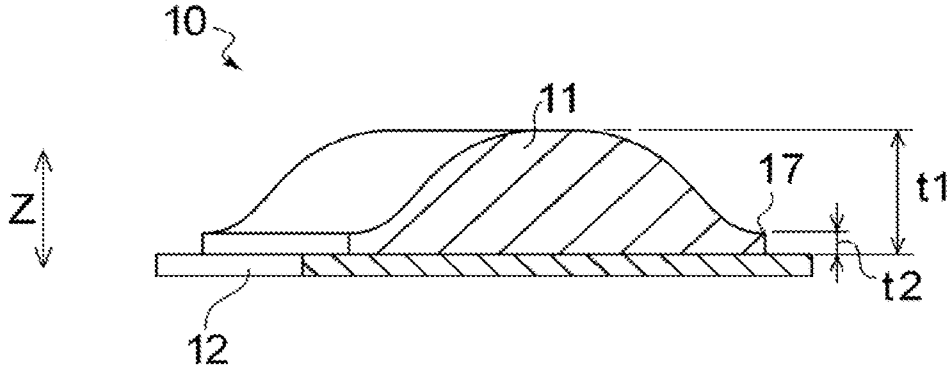
FIG. 2 is a cross-sectional view taken along the line II-II shown in FIG. 1.

The sheet layer 11 may have a uniform thickness, or may have thickness variations at different locations as shown in FIG. 2. As shown in FIG. 2, the sheet layer 11 of the present embodiment is configured such that the thickness gradually increases from a circumferential edge 17 toward the inner side of the sheet layer 11, and the surface of the sheet layer 11 is inclined when viewed in a cross section of the sheet 10 taken along a thickness direction Z of the sheet 10.

From the viewpoint of further enhancing the effect of improving the outer appearance and state of the body surface, that is, from the viewpoint of facilitating the concealing of wrinkles, spots, and the like on the body part to which the sheet 10 is applied, the maximum thickness t1 (see FIG. 2) of the sheet layer 11 is preferably 5.1 μm or more, and more preferably 10 μm or more.

Also, from the viewpoint of obtaining a sheet appearance that is less noticeable when the sheet 10 is applied to the skin, the maximum thickness t1 is preferably 500 μm or less, and more preferably 400 μm or less.

The sheet layer 11 of the present embodiment is preferably configured such that the circumferential edge 17 has a thickness smaller than that of an inner portion located on the inner side of the circumferential edge 17, and more preferably has the smallest thickness when viewed in a transverse cross section. The transverse cross section can be viewed by, for example, obtaining a cross-sectional profile curve of a three-dimensional shape, which will be described later.

From the viewpoint of making the sheet layer 11 more likely to retain the sheet state, the thickness t2 (see FIG. 2) of the circumferential edge 17 is preferably 0.3 μm or more, and more preferably 0.5 μm or more.

Also, from the viewpoint of making the boundary between the skin and the sheet less visually recognizable, the thickness t2 is 10 μm or less, preferably 9 μm or less, and more preferably 8 μm or less.

Method of Measuring Three-Dimensional Shape of Sheet Layer

The thickness t1 of the sheet layer 11 and the thickness t2 of the circumferential edge 17 of the sheet layer 11 can be obtained by measuring the three-dimensional shape of the surface of the sheet layer using a laser three-dimensional shape measurement system (for example, a combination of a measurement system EMS 2002 AD-3D available from COMS Co., Ltd. and a displacement sensor LK-2000 available from Keyence Corporation). First, the sheet 10 is set by placing the base layer on an automatic stage. Next, the sheet 10 is scanned with a laser displacement meter while the automatic stage is moved in the X axis direction, and the height of the surface of the sheet layer is measured at a predetermined measurement pitch $X_P$. Then, the automatic stage is displaced in the Y axis direction that is perpendicular to the X axis by a measurement pitch $Y_P$, and an operation of scanning the sheet 10 with the laser displacement meter while moving the automatic stage in the X axis direction and measuring the height of the surface of the sheet layer at the predetermined measurement pitch $X_P$ is repeated. In this way, data regarding the surface shape of the sheet layer is obtained. The measurement pitch $X_P$ in the X axis direction is set to 0.235 mm, the measurement pitch $Y_P$ in the Y axis direction is set to 0.350 mm, and the resolution in the height (Z axis) direction is set to 0.1 μm. Also, the range of measurement is set to a range that includes the entire sheet layer when viewed in plan view, or in other words, in the X axis direction and the Y axis direction, and the measurement pitch may be changed as appropriate according to the measurement target. The measurement described above is performed under a no-load condition. Then, the thickness of the sheet layer and the thickness of the circumferential edge of the sheet layer are measured based on the three-dimensional shape data obtained as a result of the measurement. It is assumed that the thickness of the sheet layer is the maximum thickness based on the three-dimensional shape data. Unless otherwise stated, the term "thickness" used in the description given below means a value measured based on the three-dimensional shape data. The thickness of the circumferential edge of the sheet layer 11 based on the three-dimensional shape data can be measured using the following method.

Method of Measuring Thickness of Circumferential Edge

First, a planar profile line that represents the profile shape of the sheet layer when viewed in plan view is obtained. The planar profile line may be acquired based on the three-dimensional shape data described above, or may be acquired by observing the sheet layer at magnification under a microscope or the like. For example, in the case where the sheet layer is made using nanofibers, in general, there are fibers that stick out from the surface of the sheet layer, and a fiber lean portion and a fiber rich portion are formed locally in the sheet layer. In this case, noise may be contained in a graph in which measurement values such as thickness values obtained based on the three-dimensional shape data are plotted for each position, specifically, a planar profile line. From the viewpoint of removing noise, it is preferable to perform approximation curve processing that uses polynomial approximation on the planar profile line. In the case where a plurality of approximation curves is obtained through the processing, an approximation curve that is closest to the three-dimensional shape data is selected. Next, a planar profile curve obtained by subjecting the planar profile line to approximation curve processing is fitted to the three-dimensional shape data to specify a circumferential edge of the sheet layer on the three-dimensional shape data, and the thickness of the circumferential edge is measured.

The sheet layer 11 of the present embodiment comprises a region (hereinafter also referred to as "tapered region") in which the thickness of the sheet layer 11 gradually increases from the circumferential edge 17 toward the inner side of the sheet layer 11. The tapered region can be specified as described below by obtaining a profile line on a cross section of the sheet layer 11 based on the three-dimensional shape data.

Figure 12:
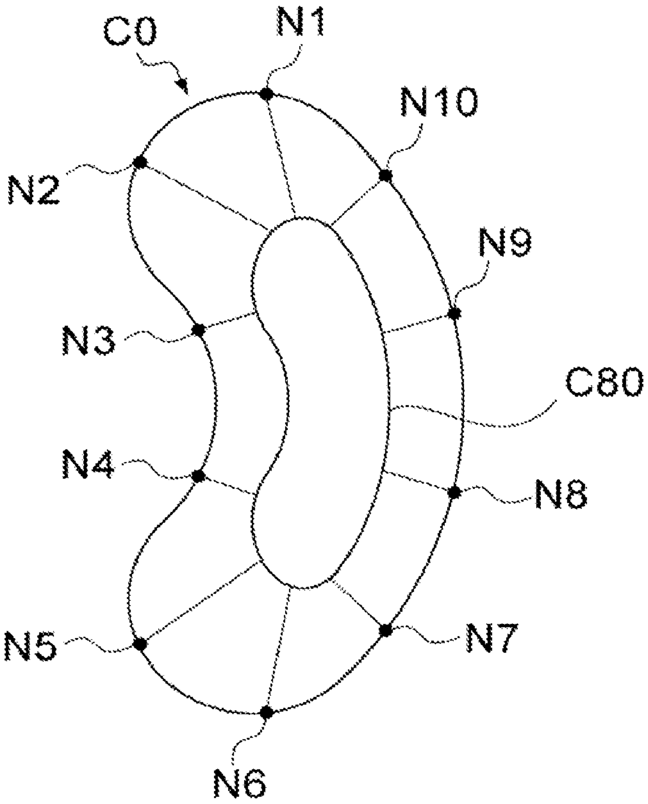
FIG. 12 is a plan view showing an example of a method for specifying a tapered region.

First, in the three-dimensional shape data, a position at which the maximum thickness is obtained is specified as an apex position, and the thickness of the sheet layer at the apex position is obtained. Next, a contour line (hereinafter also referred to as "80% thickness contour line") that represents the profile of a region whose thickness is 80% of the thickness measured at the apex position is obtained based on the three-dimensional shape data, and the position of the contour line is reflected in the three-dimensional shape data together with the planar profile curve. For example, as shown in FIG. 12, a planar profile curve C0 and an 80% thickness contour line C80 are reflected in the three-dimensional shape data. As the 80% thickness contour line, it is preferable to use a planar profile line that has undergone approximation curve processing described above. Next, a position arbitrarily selected on the planar profile curve is defined as a first point, and first to tenth points that divide the circumferential length of the planar profile curve into 10 equal parts are set on the planar profile curve. Reference numerals N1 to N10 shown in FIG. 12 are examples of the first to tenth points. Next, at each of the first to tenth points, a cross-sectional profile line of the sheet layer on the three-dimensional shape data is obtained. The cross-sectional profile line is a profile line on a cross-section formed by cutting the sheet layer on the three-dimensional shape data along a line segment that is the shortest distance that connects each of the first to tenth points on the planar profile curve and the 80% contour line when viewed in plan view. As described above, from the viewpoint of removing noise, it is preferable to perform the above-described approximation curve processing on the cross-sectional profile line at each of the first to tenth points. In each of the obtained cross-sectional profile curves, the position of the corresponding one of the first to tenth points is reflected, and the position of the circumferential edge of the sheet layer on the cross-sectional profile curve is specified. Next, in each of the obtained cross-sectional profile curves, an inclined region whose thickness gradually increases from the circumferential edge toward the inner side of the sheet layer is specified. The inclined region is, for example, a region that extends from the circumferential edge to the apex position on the cross-sectional profile curve. Examples of the pattern of gradually increasing the thickness on the cross-sectional profile curve include a pattern of linearly increasing the thickness, a pattern of increasing the thickness in a curved manner such as a sigmoid curve or an exponential function curve, a pattern of increasing the thickness in multiple stages, and the like. Then, from among the first to tenth points, the number of points at which the cross-sectional profile curve that includes the inclined region has been confirmed is counted. Where the counted number of points at which the cross-sectional profile curve that includes the inclined region has been confirmed is defined as "n", the proportion (%) of the number of cross-sectional profile curves that include the inclined region relative to the total number of the first to tenth points, that is, 10 can be determined using "$(n/10)\times100(\%)$". That is, it is possible to determine the percentage of the tapered region relative to the entire length of the circumferential edge of the sheet layer. For example, if a cross-sectional profile curve that includes the inclined region is confirmed at five points from among the first to tenth points, it is possible to determine that the sheet layer that is a measurement target has a 50% tapered region relative to the entire length of the circumferential edge of the sheet layer.

From the viewpoint of further enhancing the effect of improving the outer appearance and state of the body surface, the percentage of the region (tapered region) whose thickness gradually increases from the circumferential edge 17 toward the inner side of the sheet layer 11 relative to the entire length of the circumferential edge of the sheet layer 11 is preferably 60% or more and 100% or less, more preferably 80% or more, even more preferably 90% or more, and yet even more preferably 100%. From the same viewpoint, it is preferable that the tapered region is present extending over the entire length of the circumferential edge of the sheet layer 11.

The thickness t1 of the sheet layer 11 and the thickness t2 of the circumferential edge 17 of the sheet layer 11 can be measured using a contact-type film thickness gauge such as Litematic VL-50A (R 5 mm super hard spherical gauge head) available from Mitutoyo Corporation. The load applied to the measurement target during measurement is set to 0.01 Pa.

Figure 3:
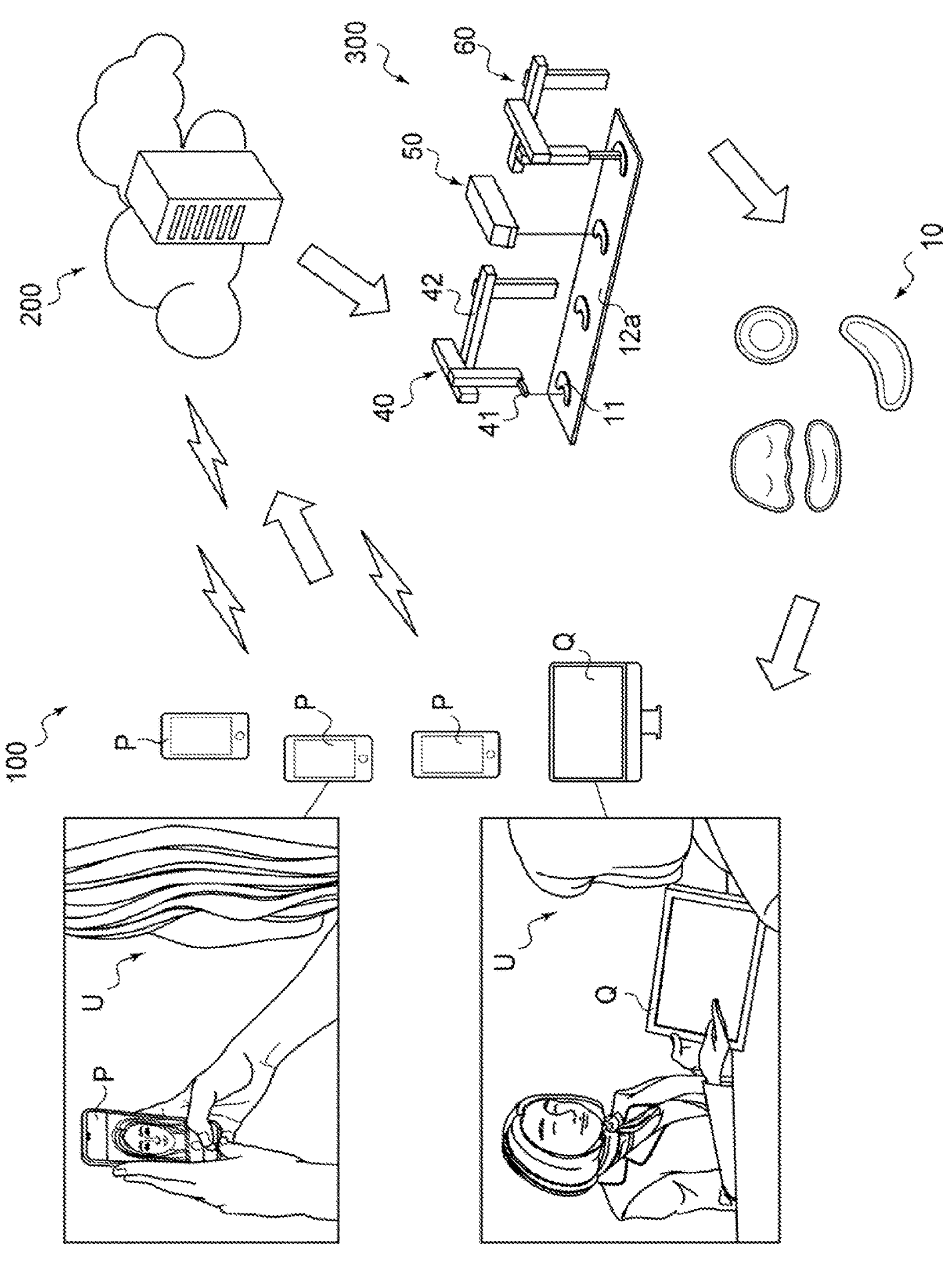
FIG. 3 is a schematic diagram showing a sheet providing method according to an embodiment of the present invention.

Next, a providing method of providing the sheet 10 will be described by way of a preferred embodiment thereof with reference to the drawings. FIG. 3 shows a schematic diagram of the providing method of the present embodiment. With the sheet providing method of the present embodiment, the sheet is provided to a user via an online-shopping type distribution channel through which a product is purchased via an electronic commerce site or a face-to-face type distribution channel through which a product is purchased via face-to-face sales at a retail store.

The sheet providing method of the present embodiment is carried out using a system 100 that is a sheet providing system according to an embodiment of the present invention. Hereinafter, the sheet providing system 100 will also be referred to simply as the "system 100". FIG. 3 shows the overall configuration of the system 100. The system 100 comprises a sheet specification determining unit 200 that carries out a determining step (A) and a sheet forming unit 300 that carries out a forming step (B).

The sheet providing method of the present embodiment comprises: a determining step (A) of determining a shape and dimensions of a sheet 10 for each individual user based on body surface information of the individual user; and a forming step (B) of forming the sheet 10 by controlling a discharge nozzle that discharges a raw material of the sheet 10 based on information regarding the shape and the dimensions of the sheet 10.

In the providing method of the present embodiment, the term "body surface information" refers to information regarding the skin of the body part to which the sheet 10 is to be applied, and includes information regarding one, two or more selected from the group consisting of the body part to which the sheet is to be applied, and a skin color, skin unevenness, skin moisture content, and skin elasticity of the body part, and preferably includes information regarding the body part. Note that information regarding skin elasticity means information regarding skin viscoelasticity.

The information regarding the body part includes measured values that indicate the surface shape of the part to which the sheet is to be applied such as the face or the lower eyelid, the size of the part, an image of the part, the skin viscoelasticity, and the like.

The information regarding the skin color is information regarding skin brightness and hue. The color information includes, in addition to the information regarding the original skin brightness and hue, information from which a color difference between a pigmented portion where pigmentation such as spots and skin dullness has occurred and a non-pigmented portion can be obtained, or in other words, information regarding the color of a discolored portion of the skin. The discolored portion includes pores, moles, and pimples. The color information includes measured values that indicate brightness and hue such as those of the L*a*b* color system, an image of the part to which the sheet is to be applied, spectroscopic properties of the skin, and the like.

The information regarding the skin unevenness is information regarding unevenness on the skin surface such as wrinkles, pores, and wounds. The unevenness information includes: measured values that indicate the depth of indentations and the height of protrusions of the skin unevenness; the size of the indentations and protrusions of the skin unevenness; an image of a portion that has the skin unevenness; the curvature of the indentations and protrusions of the skin unevenness; a measured value that indicates a pattern of the skin unevenness; an image such as an ultrasonic image that shows the elastic structure of the skin; and the like.

The information regarding the skin moisture content includes a measured value of skin moisture content, transepidermal water loss, and the like. The skin moisture content is measured using a known measuring instrument (for example, model number: CM 825 MP available from Courage+Khazaka Electronic GmbH).

The skin viscoelasticity of the skin is measured using a known measuring instrument (for example, model number: MPA 580 Dual available from Courage+Khazaka Electronic GmbH).

The brightness and hue, and the curvature of the skin unevenness, may be calculated using a known image processing method based on pixels in image data of the skin.

As will be described later, from the viewpoint of facilitating the computation processing of computing the type, shape, and size of the sheet 10, "body surface information" described above is preferably data that can be processed by a processor such as a CPU (Central Processing Unit). For example, the body surface information is preferably information (data) that is processed by the sheet providing system 100. From the same viewpoint, "body surface information" described above preferably contains image data of the body part to which the sheet is to be applied, including the part to which the sheet is to be applied, the skin color of the part, and unevenness information of the part.

The providing method of the present embodiment is intended for cosmetic purposes such as skin care and makeup, and provides, to a user, a sheet that is to be applied to the face. The determining step (A) of the present embodiment comprises: an information acquiring step (A1) of acquiring the body surface information of the individual user; and a shape and dimension determining step (A2) of determining the shape and the dimensions of the sheet 10 for the individual user based on the acquired body surface information.

In information acquiring step (A1) of the present embodiment, information regarding the surface of the face of the individual user is acquired using an information terminal P, or an apparatus Q capable of acquiring the body surface information (hereinafter also referred to as "body surface information acquiring apparatus Q").

The information terminal P is a general-purpose computer, a portable terminal, a tablet terminal, a smartphone, a wearable terminal, or the like.

The body surface information acquiring apparatus Q is an information terminal to which the body surface information can be input, an apparatus with which the state of the skin can be measured or observed, or the like. The apparatus with which the state of the skin can be measured or observed is an apparatus with which the skin moisture content, as well as the skin texture, the skin color, the skin elasticity and the like based on an enlarged image of the skin can be measured or observed, and examples include Beauty Power Scope available from Kao Corporation, Beauty Com, and the like.

Each of the information terminal P and the body surface information acquiring apparatus Q includes a CPU, a ROM (Read Only Memory), a RAM (Random Access Memory), a flash memory, a camera, a display unit, an input device with which a user performs input operations, and the like. The CPU may include a graphics processor (Graphics Processing Unit (GPU)) for displaying an image; a multimedia processor that performs encoding and decoding, such as that of a high-definition (HD) video; a display controller that performs display control; a power management integrated circuit (IC) for controlling power supply and charging; and the like. A touch panel or the like that has both the display functions and the operating functions may be used as the display units of the information terminal P and the body surface information acquiring apparatus Q. Examples of the input device include a touch panel, a keyboard, a keypad, a touchpad, a mouse, and a microphone. A user U operates the information terminal P or the body surface information acquiring apparatus Q by using the input device. The processing (for example, image processing) performed by each of the information terminal P and the body surface information acquiring apparatus Q is implemented by the CPU loading a program stored in the ROM, a disk, or the like into the RAM, and then executing the program. The processing may be implemented using an ASIC (Application Specific Integrated Circuit) or an FPGA (Field Programmable Gate Array), or a combination of an ASIC and an FPGA.

Also, the body surface information acquiring apparatus Q includes a measuring device for acquiring skin color information, skin unevenness information, skin moisture content information, and skin elasticity information. The body surface information acquiring apparatus Q may include, as the measuring device, a color-difference meter and various types of instruments described above. Furthermore, the body surface information acquiring apparatus Q may also measure the above-described brightness and hue, and curvature of the unevenness based on skin image data acquired by a camera or a microscope. In the case where such measurement is performed, a program for performing various types of image processing, such as conversion to grayscale, binarization, RGB separation, and HSV conversion, on the skin image data is implemented on the body surface information acquiring apparatus Q.

The body surface information acquired in the information acquiring step (A1) is acquired using a camera, a microscope, or a measuring device included in the information terminal P or the body surface information acquiring apparatus Q. The information terminal P or the body surface information acquiring apparatus Q may be operated by the user to which the sheet is to be applied, or a person other than the user. In this case, the above-described input device, camera, microscope, or measuring device is used to perform the operation. For example, in the case of the online-shopping type distribution channel being used, image data of the face of a user U captured using an information terminal P owned by the user U is acquired as the body surface information. In the case of the face-to-face type distribution channel being used, a result obtained by using the body surface information acquiring apparatus Q to measure or observe the state of the skin of the user is acquired as the body surface information. For example, in the case where a camera or a microscope is used, an image of the skin of the user U is acquired as the body surface information, and in the case where a measuring device is used, a measured value regarding the state of the skin of the user U that has been measured by a detector, such as a sensor, included in the measuring device is acquired as the body surface information. The camera, the microscope, or the measuring device included in the body surface information acquiring apparatus Q may also be operated by a person other than the user, such as a salesperson.

In the shape and dimension determining step (A2) of the present embodiment, the shape and the dimensions of the sheet 10 suited to the user U are determined based on the body surface information of the user U acquired in the information acquiring step (A1). Specifically, the shape and dimension determining step (A2) comprises: a shape selecting step (A2-1) of prompting the user to select a sheet shape; a position and size determining step (A2-2) of prompting the user to determine an application position of the sheet and a size of the sheet; and a determination processing step (A2-3) of determining the shape and the dimensions of the sheet suited to the user based on the body surface information, the sheet type, and information regarding the application position of the sheet and the size of the sheet determined by the user U. These steps (A2-1) to (A2-3) will be described with reference to FIGS. 4 and 5 by taking an example in which the body surface information is acquired using an information terminal P that has a camera and a touch panel function. In the shape selecting step (A2-1) to the step (A2-3), the user U determines (selects) the sheet type, the application position of the sheet, and the size of the sheet desired by the user U. At this time, the user U operates the information terminal P while referring to image data of the face of the user U that has been acquired by the camera of the information terminal P. The information terminal P transmits information regarding the application position of the sheet and the size of the sheet based on the information input through this operation to the sheet specification determining unit 200 included in the system 100 via a network (N). The sheet specification determining unit 200 of the system 100, which will be described later, is a cloud server.

The network means all information communication networks that use telecommunication technologies, and examples include a wireless or wired LAN (Local Area Network), such as a LAN, and an internet network, as well as a telephone communication network, a fiber-optic communication network, a cable communication network, and a satellite communication network.

Figure 4:
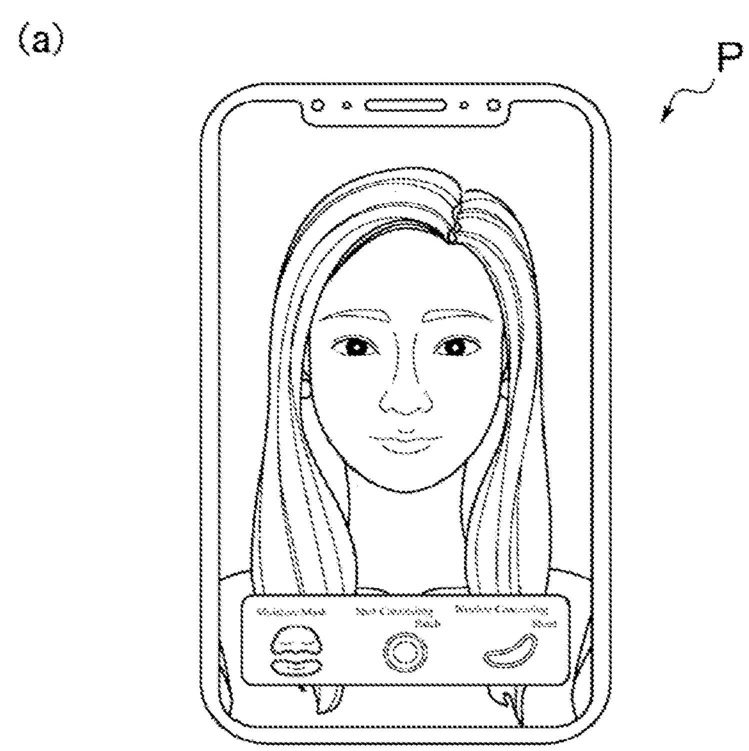
FIGS. 4(*a*) and 4(*b*) are diagrams showing an example of an operation screen displayed on a display unit of an information terminal according to the sheet providing method shown in FIG. 3.
Figure 4:
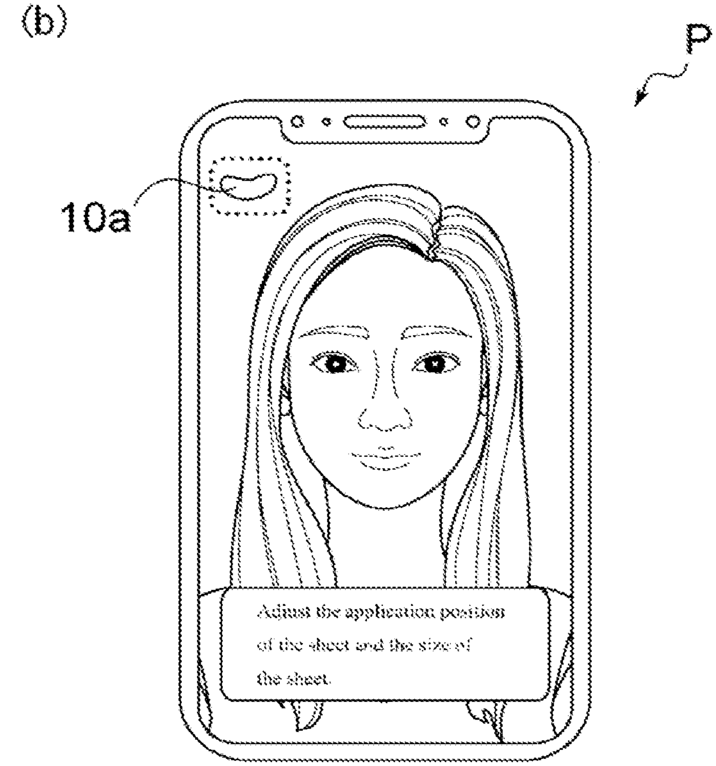

In the shape selecting step (A2-1), the sheet specification determining unit 200 displays a selection operation screen for the user U to select a sheet type based on the image data of the face of the user U, and prompts the user U to select a sheet type. Thus, the user U selects a sheet shape. For example, as shown in FIG. 4(*a*), the sheet specification determining unit 200 displays the selection operation screen on the display unit of the information terminal P. In the shape selecting step (A2-1), the sheet specification determining unit 200 may present information indicating the functions and properties of the sheet to the user U, together with the sheet shape (sheet type), and then prompt the user U to select a sheet shape. The information indicating the functions and properties of the sheet includes text of "moisture mask", "spot concealing patch", and "wrinkle concealing sheet" as shown in FIG. 4(*a*). The user U selects a sheet with a shape desired by the user U from among a plurality of types of sheets presented on the selection operation screen. Alternatively, a configuration may be used in which the user U takes, in advance, counselling on the purpose of application of the sheet and skin issues via the information terminal P, and one or more candidate sheets selected based on the result of the counselling are presented on the selection operation screen for the user U to select from among the candidate sheets. The counselling is performed using a cosmetic questionnaire, and the candidate sheets to be presented to the user U are selected as appropriate according to the responses to the questionnaire. In the present embodiment, the sheet specification determining unit 200 presents a plurality of types of sheets, performs counselling, and presents candidate sheets based on the result of the counselling.

Figure 5:
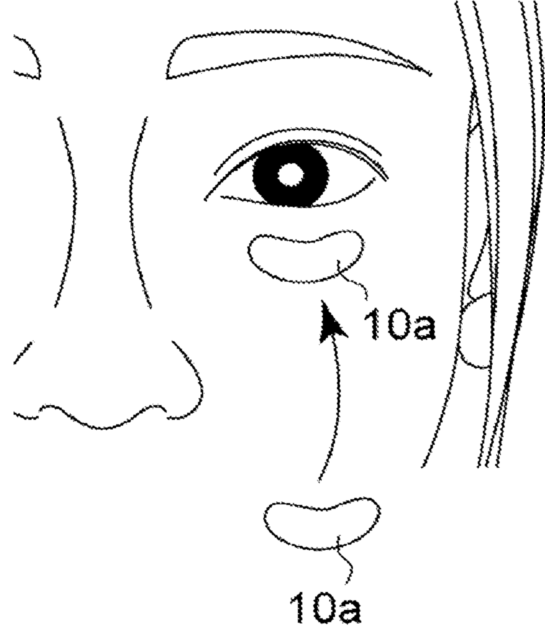
FIGS. 5(*a*) and 5(*b*) are diagrams showing details of an example of operations performed in FIG. 4(*b*).
Figure 5:
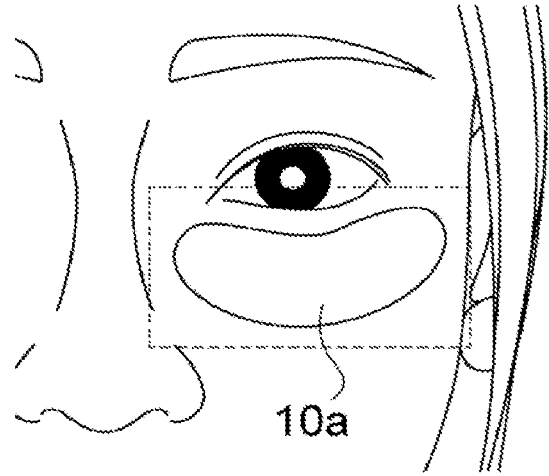

In the position and size determining step (A2-2), an adjustment operation screen is displayed for the user U to determine the application position and the size of the sheet selected by the user U in the shape selecting step (A2-1), and then the user U is prompted to determine the application position and the size of the sheet. For example, as shown in FIG. 4(*b*), the sheet specification determining unit 200 displays the adjustment operation screen on the display unit of the information terminal P. FIG. 4(*b*) shows the initial state of the adjustment operation screen. The user U places a sheet 10*a* on a desired position on the face displayed on the adjustment operation screen so as to determine the application position of the sheet 10*a*. Specifically, as shown in FIG. 5(*a*), the user U selects the sheet 10*a* displayed on the adjustment operation screen, drags the sheet to the desired position on the face, and determines the application position of the sheet 10*a*. Next, in order to determine an appropriate size of the sheet 10*a* placed at the determined application position, the sheet specification determining unit 200 prompts the user U to determine a desired size of the sheet. Specifically, as shown in FIG. 5(*b*), the user U determines the desired size of the sheet 10*a* by pinching in or out on the screen to reduce or expand the sheet 10*a* at the application position. Regarding the operations shown in FIGS. 5(*a*) and 5(*b*), the sheet specification determining unit 200 displays, on the display unit of the information terminal P, a message prompting the user U to determine the application position and the size of the sheet shown on the image.

The operations performed by the user U in the shape selecting step (A2-1) and the position and size determining step (A2-2) may be performed by a person other than the user U such as, for example, a salesperson in face-to-face sales. In this case, the person other than the user U performs the operation of selecting a sheet and the operation of adjusting the application position and the size of the sheet according to the wishes of the user U. In the case where the above-described counselling is performed, a person other than the user U performs operations necessary for counselling.

Information regarding the sheet shape, the application position and the size of the sheet on the image determined by the user U in the shape selecting step (A2-1) and the position and size determining step (A2-2) is transmitted to the sheet specification determining unit 200 via a network. The sheet specification determining unit 200 collects the information from each of a plurality of users via the information terminals P or the body surface information acquiring apparatus Q, and stores the collected information in a storage unit, which will be described later.

In the determination processing step (A2-3), the sheet specification determining unit 200 calculates the shape and the dimensions of the sheet suited to the user based on the information regarding the sheet type, the application position and the size of the sheet determined by the user U in the shape selecting step (A2-1) and the position and size determining step (A2-2) and the information regarding the surface of the face, and then determines the shape and the dimensions of the sheet. Specifically, the sheet specification determining unit 200 derives the dimensions of the sheet, or calculates the size (actual size) of the face of the user U, based on the image data of the user U, and further derives, based on the size of the face, dimensions of the sheet that correspond to the application position and the size of the sheet determined by the user U. The processing method for performing the above-described derivation is executed by a sheet size computing unit 245, which will be described later. Information regarding the derived dimensions of the sheet is transmitted from the sheet specification determining unit 200 to the sheet forming unit 300.

The providing method of the present embodiment includes a step of optimizing the shape and the dimensions of the sheet determined in the determination processing step (A2-3) through machine learning that uses learning data stored in the sheet specification determining unit 200. The machine learning processing in this step is carried out by an information utilization unit 26, which will be described later. A detailed description of machine learning will be given in relation to the description of the information utilization unit 26.

In the forming step (B), the sheet forming unit 300 included in the system 100 forms a sheet by controlling a discharge nozzle that discharges the raw material of the sheet 10 based on the information regarding the shape and the dimensions of the sheet determined in the determination processing step (A2-3). The sheet forming unit 300 includes a sheet layer forming apparatus 40, a cutting apparatus 50, and a handling apparatus 60 (see FIG. 3). The sheet layer forming apparatus 40, the cutting apparatus 50, and the handling apparatus 60 are all controlled by a production control unit 35 that is also included in the sheet forming unit 300. The production control unit 35 will be described later in detail in relation to the description of the system 100.

The sheet layer forming apparatus 40 includes a discharge nozzle 41 for discharging the raw material, and a sheet layer 11 is formed as a result of the raw material being discharged from the discharge nozzle 41 onto a continuous sheet 12*a* of the base layer. The discharge nozzle 41 is controlled based on the information regarding the shape and the dimensions of the sheet. As used herein, the term “control” means to control one, two or more selected from the group consisting of the discharge amount of the raw material, the discharge position of the raw material, and a movement trajectory of the discharge nozzle 41, which will be described later, so as to achieve the shape and the dimensions of the sheet determined in the determination processing step (A2-3). For example, a production apparatus disclosed in JP 2020-090769A or JP 2020-045591A can be used as the sheet layer forming apparatus 40.

The cutting apparatus 50 cuts the continuous sheet 12*a* of the base layer along the profile (the circumferential edge 17) of the sheet layer 11 formed by the sheet layer forming apparatus 40 or at a position spaced apart from the profile of the sheet layer 11 toward the outer side of the sheet. A laser cutter, or a cutting apparatus that includes a cutting head including a cutter, a slider that holds the cutting head, and an XY rail stage that is capable of moving the slider in a planar direction can be used as the cutting apparatus 50.

The handling apparatus 60 takes out a sheet 10 obtained through cutting performed by the cutting apparatus 50. A manipulator that includes a robot hand at a distal end of an arm can be used as the handling apparatus 60.

In the case where the sheet is provided via the online-shopping type distribution channel, the sheet production in the forming step (B) is carried out at a sheet production business location. Identification information of the user U is assigned to the produced sheet 10, and the produced sheet 10 is packed in a package or the like. Delivery destination information of the user U is attached to the package or the like, and the package or the like is then delivered to the user U. Accordingly, the sheet 10 is provided to the user U.

In the case where the sheet is provided via the face-to-face type distribution channel, the sheet production in the forming step (B) may be carried out at a sheet production business location. In this case, the produced sheet 10 is provided to the user U via a store such as a retail store. Alternatively, the sheet production in the forming step (B) may be carried out in a store. In this case, the sheet layer forming apparatus 40, the cutting apparatus 50, and the handling apparatus 60 are installed in the store, and a sheet 10 is produced in parallel to face-to-face sales such as counselling using the body surface information acquiring apparatus Q, and the sheet 10 is provided directly to the user who is a customer at the store.

The providing method of the present embodiment includes the determining step (A) and the forming step (B) described above, and it is therefore possible to provide, to the user U, a custom-made sheet 10 determined according to the wishes of the user U. In particular, with the determining step (A), the wishes of the user U can be reflected in the shape and the dimensions of the sheet via an interaction means, such as the internet or a GUI, and it is therefore possible to realize a sheet that meets the expectations of the user U. In addition, in the forming step (B), a sheet layer is formed by controlling the discharge nozzle 41, and it is therefore possible to form sheets of various types of shapes. As a result, it is possible to fulfil a wide variety of user needs. That is, with the determining step (A) and the forming step (B) described above, it is possible to provide, to each individual user, a sheet that has a shape and dimensions suited to the individual user. Also, the sheet providing method of the present embodiment is effective in carrying out the one-to-one production technique for sheet products.

The providing method of the present embodiment is configured to form a sheet by controlling the discharge nozzle 41, but a sheet 10 that has a shape and dimensions suited to for each user may be formed by controlling the cutting apparatus 50 instead of, or in addition to, the discharge nozzle 41. For example, a sheet of a desired shape may be formed by cutting out a sheet from a continuous stacked sheet in which a continuous sheet of the sheet layer 11 and a continuous sheet of the base layer 12 are stacked while moving a cutting means such as a laser relative to the continuous stacked sheet based on the information regarding the shape and the dimensions of the sheet. In this case as well, the advantageous effects described above can be obtained. As the cutting means, it is possible to use, other than a laser, for example, a known cutting apparatus such as a cutting apparatus that includes a cutter roll that has a circumferentially extending cutting blade on the circumferential surface of the roll and an anvil roll that receives the blade of the cutter roll, or an ultrasonic cutter.

The sheet layer forming apparatus 40 used in the present embodiment will be described in detail. The sheet layer forming apparatus 40 comprises the discharge nozzle 41 and a moving device 42 that moves the discharge nozzle 41. The moving device 42 included in the sheet layer forming apparatus 40 is configured to be capable of moving the discharge nozzle 41 in a planar direction. For example, the moving device 42 comprises: a slider that holds the discharge nozzle 41; and rails that extend in the X axis direction and the Y axis direction, respectively. As a result of the slider moving along the rails, the discharge nozzle 41 can be moved in the X axis direction and the Y axis direction, or in other words, in the planar direction. The moving device 42 also comprises a Z-axis rail that extends in the Z axis direction that is a vertical direction perpendicular to the X axis direction and the Y axis direction. As a result of the slider moving along the Z-axis rail, the discharge nozzle 41 can be moved in the Z axis direction, or in other words, up and down in the vertical direction. As described above, with the moving device 42, the discharge nozzle 41 can be moved freely in the X axis direction, the Y axis direction, and the Z axis direction. The moving device 42 is controlled by the production control unit 35. The sheet layer forming apparatus 40 forms a sheet layer 11 that has a predetermined shape and dimensions by discharging a raw material liquid that contains the raw material of the sheet layer 11 from the discharge nozzle 41 while moving the discharge nozzle 41. That is, in the forming step (B), the sheet forming unit 300 forms a sheet 10 by moving the discharge nozzle 41 along a trajectory that is set based on the information regarding the shape and the dimensions of the sheet determined in the determination processing step (A2-3) while discharging the raw material from the discharge nozzle 41. This is preferable from the viewpoint of further realizing a sheet that has a shape and dimensions in which the wishes of the user are reflected. The movement trajectory of the discharge nozzle 41 is a trajectory that extends along the shape in plan view of the sheet layer 11, but such a trajectory can be set using, for example, software such as an SEL generator (available from IAI Corporation).

According to the sheet providing method of the present embodiment, a sheet that has a two-dimensional shape desired by the user can be formed by controlling the movement trajectory of the discharge nozzle 41. From the viewpoint of forming a sheet that has a desired three-dimensional shape, it is preferable that the sheet providing method is configured to form a sheet 10 by controlling either one or both of the discharge amount of the raw material from the discharge nozzle 41 and the movement trajectory of the discharge nozzle 41 based on the information regarding the shape and the dimensions of the sheet. The three-dimensional shape of the sheet can be easily controlled by partially changing the thickness by either changing the discharge amount of the raw material or overlapping the movement trajectory of the discharge nozzle 41.

From the viewpoint of easily forming a sheet layer 11 that has a desired three-dimensional shape, it is preferable that the sheet layer 11 is made using nanofibers. The sheet layer forming apparatus 40 of the present embodiment is a known electrospinning apparatus that forms a sheet layer 11 by discharging a raw material while applying a voltage. The sheet layer forming apparatus 40 deposits, on the continuous sheet 12*a* of the base layer, nanofibers formed from a raw material liquid that contains the raw material of the sheet layer 11 using an electrospinning method. The sheet layer 11 thus obtained is made of fibers (nanofibers) formed from the raw material. Nanofibers are fibers that have an extremely small fiber diameter.

From the viewpoint of facilitating the formation of a sheet, the nanofibers have, when the fiber diameter is expressed as circle-equivalent diameter, a fiber diameter of 0.1 μm or more, and preferably 0.5 μm or more.

Also, from the viewpoint of improving the conformability of the sheet on the skin when the sheet is applied to the skin, the nanofibers have a fiber diameter of 6 μm or less, preferably 4 μm or less, more preferably 2 μm or less, and even more preferably 1 μm or less.

The fiber diameter of the fibers is an average fiber diameter obtained by, for example, arbitrarily selecting 300 fibers, excluding defects such as masses of fibers, fiber intersections, and polymer droplets, from a two-dimensional image obtained through observation under a scanning electron microscope (SEM), defining the length of a line perpendicular to the lengthwise direction of a fiber as the fiber diameter, and calculating the arithmetic mean value of the fiber diameter of 300 fibers.

The sheet layer forming apparatus 40 can produce the sheet layer 11 so as to have a region (tapered region) whose thickness gradually increases from the circumferential edge toward the inner side of the sheet layer 11. A sheet layer 11 that has such a three-dimensional shape is unlikely to be visually recognized in a state in which it is applied to the skin. The sheet layer 11 that has a thickness variation as described above preferably has a thickness within the above-described range.

The sheet layer 11 that has a tapered region, or in other words, the sheet layer 11 that has a thickness variation, can be formed by controlling either one or both of the discharge amount of the raw material from the discharge nozzle 41 and the movement trajectory of the discharge nozzle 41, so as to change the deposition amount of nanofibers to be different for each position, or in other words, to adjust the deposition distribution of nanofibers. The method of producing the sheet layer 11 that has a tapered region will be described below in detail. The production method includes: a trajectory calculation step of determining a movement trajectory of the discharge nozzle 41; and a deposition step of depositing a raw material (nanofibers) based on the movement trajectory. In the present embodiment, the trajectory calculation step is carried out by a production data deriving unit 33, and the deposition step is carried out by the sheet layer forming apparatus 40.

In the trajectory calculation step, the movement trajectory of the discharge nozzle 41 is determined based on the correlation between a factor relating to the deposition distribution of nanofibers and the thickness of the deposited nanofibers. The movement trajectory is a trajectory for forming a sheet layer 11 that has a tapered region and also has a predetermined shape in plan view and a predetermined thickness. As used herein, "predetermined shape in plan view" is determined based on the information regarding the shape and the dimensions of the sheet determined in the determination processing step (A2-3). "Predetermined thickness" is a setting value that is determined according to the product specifications or the like based on the functions and properties of the sheet, and may be the minimum or maximum thickness of the sheet layer 11, or may be the minimum or maximum thickness of the tapered region.

The deposition distribution of nanofibers in the trajectory calculation step is a distribution of the deposition amount of nanofibers deposited on the continuous sheet 12*a* of the base layer. The factor relating to the deposition distribution of nanofibers may include, for example, the moving speed of the discharge nozzle 41, the discharge speed of the raw material liquid, the potential difference between the discharge nozzle 41 and the continuous sheet 12*a* of the base layer, the distance between the discharge nozzle 41 and the continuous sheet 12*a* of the base layer, the inner diameter of the discharge nozzle 41, the material of the discharge nozzle 41, and the like, and one, two or more selected from these may be combined. With each of the factors described above, by adjusting the numerical value of the factor, the thickness of the sheet layer composed of nanofibers can be increased or decreased.

For example, in the case where, as the factors relating to the deposition distribution of nanofibers, the moving speed of the discharge nozzle 41 (hereinafter also referred to as "factor a"), the discharge speed of the raw material liquid (hereinafter also referred to as "factor b"), and the distance between the discharge nozzle 41 and the continuous sheet 12*a* of the base layer (hereinafter also referred to as "factor c") are used, with the moving speed of the discharge nozzle 41 (the factor a) and the discharge speed of the raw material liquid (the factor b), the deposition amount of nanofibers per unit area can be increased or decreased, as a result of which, the thickness of deposited nanofibers can also be increased or decreased accordingly. Also, with the distance between the discharge nozzle 41 and the continuous sheet 12*a* of the base layer (the factor c), the area of a deposit of nanofibers per unit time can be increased or decreased. As described above, the factors a to c are factors that change the deposition distribution of nanofibers.

In the trajectory calculation step, a trajectory is set in which the correlation between the factors a to c and the thickness of the deposit of nanofibers is reflected in the predetermined shape in plan view, or in other words, the shape in plan view of the sheet layer 11 based on the information regarding the shape and the dimensions of the sheet determined in the determination processing step (A2-3). The correlation is obtained by setting each factor relating to the deposition distribution of nanofibers to a predetermined value, making a test sample of nanofibers while moving the discharge nozzle 41 along a predetermined trajectory, and measuring the thickness distribution of the test sample, and is usually obtained in advance prior to the production of the sheet layer 11. For example, the correlation can be obtained in the following manner. The factors a to c are set to predetermined values, and a test sample of nanofibers is made while moving the discharge nozzle 41 in one direction. For the test sample, data (hereinafter also referred to as "simulation data") regarding the thickness in a cross section perpendicular to the extending direction of the test sample is acquired. Such simulation data is obtained through measurement using, for example, the laser three-dimensional shape measurement system described above. The thickness of nanofibers to be formed is simulated based on the simulation data and the shape in plan view (the predetermined shape in plan view) of the sheet layer 11, and then a movement trajectory is determined. As the simulation data, data obtained by setting the factors a to c to setting values of the same condition, or a plurality of pieces of data obtained by setting the factors relating to the deposition distribution of nanofibers to different setting values may be used.

In the trajectory calculation step, calculation is performed such that the predetermined thickness of the resulting nanofiber sheet reaches the setting value by adjusting the numerical values of the factors relating to the deposition distribution of nanofibers (for example, the factors a to c), or forming, on the movement trajectory, a portion in which the deposition position of nanofibers is overlapped, or a portion in which the deposition position of nanofibers is not overlapped. Also, the movement trajectory obtained as a result of calculation is a trajectory that has a portion that extends along the shape in plan view (the predetermined shape in plan view) of the sheet layer 11 based on the information regarding the shape and the dimensions of the sheet determined in the determination processing step (A2-3). Such a trajectory can be set using, for example, software such as the SEL generator described above. In the movement trajectory calculation step, the calculation of the movement trajectory, or in other words, the simulation of the movement trajectory is repeatedly performed until a movement trajectory that has a portion that extends along the predetermined shape in plan view and satisfies a condition in which the thickness of nanofibers reaches a predetermined numerical value is obtained.

The movement trajectory determined in the trajectory calculation step may be, for example, a combination of a trajectory group that includes a plurality of nested trajectories with substantially similar shapes and crossovers that connect the plurality of trajectories, a unicursal linear trajectory, or the like.

In the deposition step, nanofibers are deposited while moving the discharge nozzle 41 based on the movement trajectory determined in the trajectory calculation step. In the present embodiment, data regarding the movement trajectory determined in the trajectory calculation step is transmitted to the production control unit 35, and the moving device 42 is activated based on an operation signal transmitted from the production control unit so as to move the discharge nozzle 41 along the movement trajectory. In this way, by moving the discharge nozzle 41 along the movement trajectory, it is possible to form a nanofiber layer that has the predetermined shape in plan view and the thickness simulated during setting of the movement trajectory.

The providing method of the present embodiment is configured to provide a sheet composed of nanofibers, but it is possible to provide a coating-formable sheet without any particular limitation. The term "coating-formable" includes being able to form a coating by spreading a raw material in a liquid state and then drying the raw material, or being able to form a coating by depositing nanofibers that contain a fiber-formable polymer compound. From the viewpoint of outer appearance, adhesion, and the like of the sheet when the sheet is applied to the skin, the sheet is preferably a coating formed of a deposit of nanofibers, or a coating that contains a deposit of nanofibers.

Examples of the coating-formable polymer compound include a silicone-based polymer material, an acrylic polymer material, a vinyl-based polymer material, a condensation polymer material, a fluorine-containing polymer material, and the like. These polymer-based materials can be used alone or in a combination of two or more.

Examples of the silicone-based polymer material include a poly(N-acyl alkyleneimine)-modified silicone, a sugar-modified silicone (JP S63-139106A), a polyglycerin-modified silicone (JP 2004-339244A), a polyamino acid-modified silicone (JP 2002-145724A), a silicone-grafted acrylate polymer (JP H4-342513A), a silicone PEG block polymer (JP H4-234307A), and the like.

The acrylic polymer material may be, for example, a (co)polymer of a monomer that contains one, two or more monomers selected from acrylic acid and derivatives thereof, methacrylic acid and derivatives thereof, crotonic acid and derivatives thereof, acrylamide, acrylalkylamide, acrylonitrile, diacetone acrylamide, and methacrylamide.

The vinyl-based polymer material may be, for example, a (co)polymer of a monomer that contains one, two or more monomers selected from eicosene, vinyl chloride, vinyl acetate, styrene, vinyl neodecanoate, vinyl acetaldiethylamino acetate, vinyl pyrrolidone, vinyl butyral, butadiene, and hexadecene.

The condensation polymer material may be, for example, a product produced through a condensation reaction of an acid with an alcohol or an alcohol derivative, or a modified product thereof. As the acid, for example, one, two or more selected from maleic anhydride, phthalic acid, itaconic acid, citraconic anhydride, phthalic anhydride, isophthalic acid, terephthalic acid, tetrahydrophthalic anhydride, succinic acid, adipic acid, sebacic acid, tetrachlorophthalic anhydride, and HET acid may be used.

As the alcohol or the alcohol derivative, for example, one, two or more selected from ethylene glycol, diethylene glycol, triethylene glycol, propylene glycol, dipropylene glycol, 1,3-butanediol, 2,3-butanediol, glycerin, pentaerythritol, trimethylolpropane, and epichlorohydrin may be used.

As the fluorine-containing polymer material, for example, one, two or more selected from a polytetrafluoroethylene resin, a stearyl methacrylate/perfluoroalkyl methacrylate copolymer (JP H4-100534A), and a fluorine-modified silicone (JP H9-67240A) may be used.

As the raw material of the nanofibers, a water-insoluble polymer compound, a water-soluble polymer compound, or the like may be used.

Examples of the water-insoluble polymer compound include: a completely saponified polyvinyl alcohol that can be insolubilized after being formed into nanofibers; a partially saponified polyvinyl alcohol that can be cross-linked using a cross-linking agent together after being formed into nanofibers; oxazoline-modified silicones such as a poly(N-propanoylethyleneimine) graft-dimethylsiloxane/γ-aminopropylmethyl siloxane copolymer; zein (the main component of corn protein); polyester resins such as polylactic acid (PLA), polyethylene terephthalate resin, and polybutylene terephthalate resin; acrylic resins such as polyacrylonitrile resin and polymethacrylate resin; polyamide resins such as polystyrene resin, polyvinyl butyral resin, polyurethane resin, and nylon; polyimide resin; polyamide imide resin; and the like. These water-insoluble polymer compounds can be used alone or in a combination of two or more.

Examples of the water-soluble polymer compound include: mucopolysaccharides such as pullulan, hyaluronic acid, chondroitin sulfuric acid, poly-γ-glutamic acid, modified corn starch, β-glucan, gluco-oligosaccharide, heparin, and keratosulfate; natural polymers such as cellulose, pectin, xylan, lignin, glucomannan, galacturon, psyllium seed gum, tamarind seed gum, gum arabic, gum tragacanth, water-soluble soybean polysaccharide, alginic acid, carrageenan, laminaran, agar (agarose), fucoidan, methyl cellulose, hydroxypropyl cellulose, and hydroxypropyl methyl cellulose; synthetic polymers such as a partially saponified polyvinyl alcohol (in the case where a cross-linking agent is not used together), a low saponified polyvinyl alcohol, polyvinylpyrrolidone (PVP), polyethylene oxide, water-soluble nylon, water-soluble polyester, and sodium polyacrylate; and the like. These water-soluble polymer compounds can be used alone or in a combination of two or more.

The sheet layer 11 may contain an additional polymer compound other than the coating-formable polymer compound, and may further contain an additional component.

Examples of the additional polymer compound include polypropylene, polyethylene, polystyrene, polyvinyl alcohol, polyurethane, polyethylene oxide, polyethylene terephthalate, polybutylene terephthalate, polyethylene naphthalate, poly-m-phenylene terephthalate, poly-p-phenylene isophthalate, polyvinylidene fluoride, a polyvinylidene fluoride-hexafluoropropylene copolymer, polyvinyl chloride, a polyvinylidene chloride-acrylate copolymer, polyacrylonitrile, a polyacrylonitrile-methacrylate copolymer, polycarbonate, polyarylate, polyester carbonate, nylon, aramid, polycaprolactone, polylactic acid, polyglycolic acid, collagen, polyhydroxy butyrate, polyvinyl acetate, polypeptide, and the like.

As the additional component, a component that is used as a cosmetic material can be used. Examples include a medicinal component, a moisturizing component, various types of vitamins, an aromatic compound, an ultraviolet protection agent, a surfactant, a color pigment, an extender pigment, a dye, a stabilizer, an antiseptic, an antioxidant, and the like. These components can be used alone or in a combination of two or more.

The sheet layer 11 is formed by discharging a raw material liquid that contains a coating-formable raw material from the discharge nozzle. The raw material liquid may contain, in addition to the components described above, a solvent, inorganic particles, organic particles, a plant extract, a surfactant, an oil, an electrolyte for adjusting ion concentration, and the like, as needed.

Examples of the solvent include water, methanol, ethanol, 1-propanol, 2-propanol, hexafluoroisopropanol, tetraethylene glycol, triethylene glycol, dibenzyl alcohol, 1,3-dioxolane, 1,4-dioxane, methyl ethyl ketone, methyl isobutyl ketone, methyl-n-hexyl ketone, methyl-n-propyl ketone, diisopropyl ketone, diisobutyl ketone, acetone, hexafluoro acetone, phenol, formic acid, methyl formate, ethyl formate, propyl formate, methyl benzoate, ethyl benzoate, propyl benzoate, methyl acetate, ethyl acetate, propyl acetate, dimethyl phthalate, diethyl phthalate, dipropyl phthalate, methyl chloride, ethyl chloride, methylene chloride, chloroform, o-chlorotoluene, p-chlorotoluene, carbon tetrachloride, 1,1-dichloroethane, 1,2-dichloroethane, trichloroethane, dichloropropane, dibromoethane, dibromopropane, methyl bromide, ethyl bromide, propyl bromide, acetic acid, benzene, toluene, hexane, cyclohexane, cyclohexanone, cyclopentane, o-xylene, p-xylene, m-xylene, acetonitrile, tetrahydrofuran, N,N-dimethyl formamide, pyridine, and the like.

As the base layer 12, for example, a synthetic resin film made of a polyolefin resin or a polyester resin, a fiber sheet such as a woven fabric, a knit, or a non-woven fabric, or a foam such as a sponge can be used. As the base layer 12, from the viewpoint of releasability of the sheet layer, it is preferable to use a fiber sheet such as a non-woven fabric, a foam such as a sponge, or a synthetic resin film with a rough surface.

Figure 6:
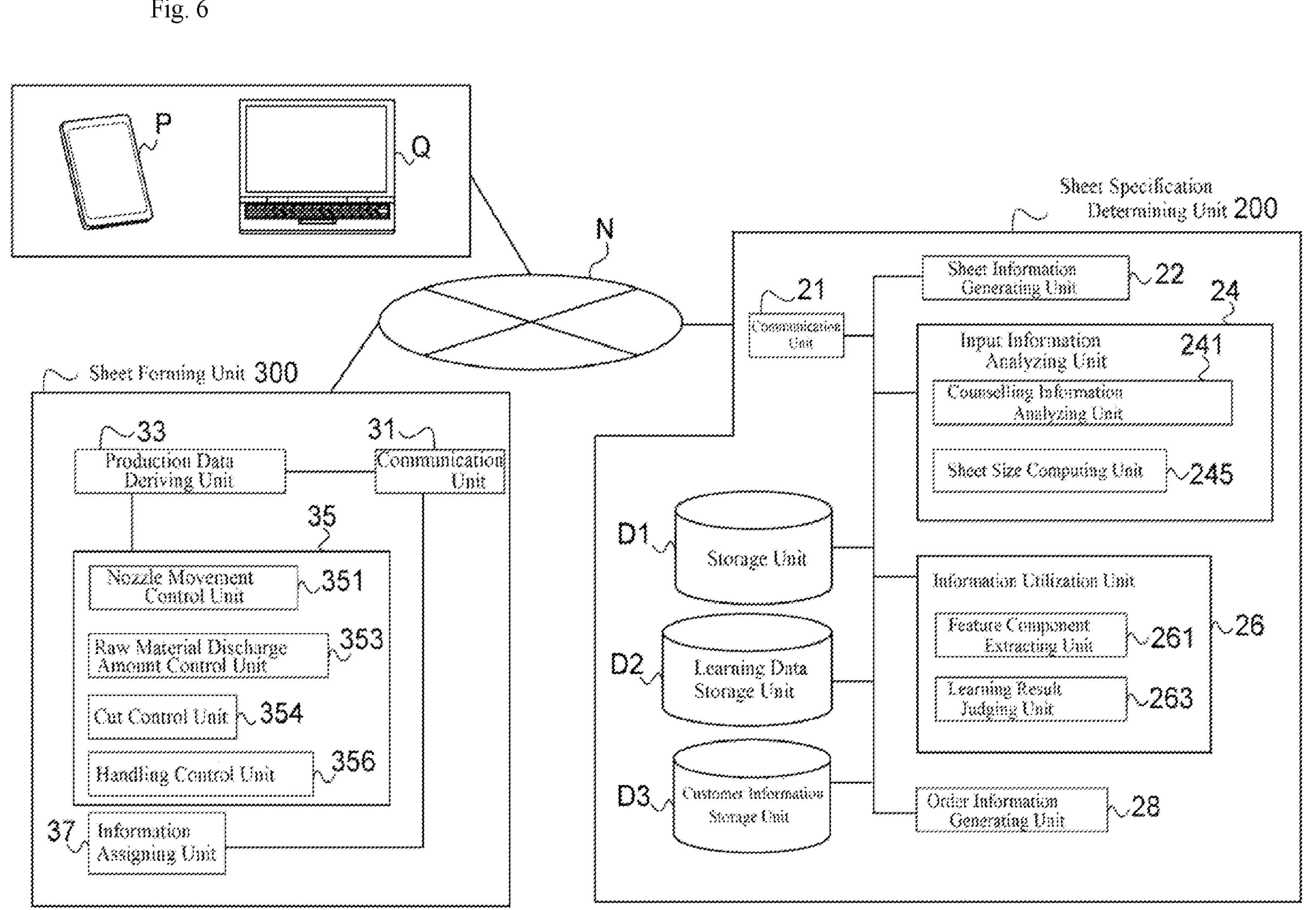
FIG. 6 is a block diagram showing a sheet providing system according to an embodiment of the present invention.

Next, the system 100 will be described in detail. The system 100 is a sheet providing system according to an embodiment of the present invention, and is preferably used to perform the sheet providing method according to the present invention. FIG. 6 shows a block diagram of the system 100.

The system 100 includes the sheet specification determining unit 200 and the sheet forming unit 300 that were described above. As the sheet specification determining unit 200 and the sheet forming unit 300, a known general-purpose computer can be used. The general-purpose computer includes a CPU, a ROM, a RANI, an HDD (Hard Disk Drive), and the like. The processing performed by the sheet specification determining unit 200 and the sheet forming unit 300 is implemented by the CPU loading a program stored in the ROM, a disk or the like into the RAM, and then executing the program. The processing may be implemented using an ASIC (Application Specific Integrated Circuit), an FPGA (Field Programmable Gate Array), or a combination of an ASIC and an FPGA.

Alternatively, instead of providing software and hardware dedicated for the system 100, an OS (Operating System) such as on-premise sever configuration, and the like in the sheet specification determining unit 200, a SaaS (Software as a Service), a PaaS (Platform as a Service), or an IaaS (Infrastructure as a Service) that uses a cloud server may be used.

The sheet specification determining unit 200 is connected to the information terminals P and the body surface information acquiring apparatus Q that were described above via a network N. The sheet specification determining unit 200 is connected to the sheet forming unit 300 via the network N. In the present embodiment, an application (hereinafter referred to as an "app") used in the system 100 has been installed on the information terminals P and the body surface information acquiring apparatus Q. Exchange of information between the sheet specification determining unit 200 and each information terminal P may be performed via a general-purpose web browser.

In the present embodiment, the sheet specification determining unit 200 is a cloud server, and the sheet forming unit 300 is a general-purpose computer installed at a sheet production location for producing sheets (see FIG. 3).

As shown in FIG. 6, the sheet specification determining unit 200 includes a communication unit 21, a sheet information generating unit 22, an input information analyzing unit 24, an information utilization unit 26, an order information generating unit 28, a storage unit D1, a learning data storage unit D2, and a customer information storage unit D3.

The communication unit 21 receives access information and stores the information in the storage unit D1. The access information is information used to make access from each of the plurality of information terminals P and the body surface information acquiring apparatus Q, and includes information required for computation and processing performed by the sheet specification determining unit 200 such as acquiring data, generating data, and updating data. Specifically, the access information includes the body surface information (for example, image data) of individual users, information regarding terminal operations performed by the user U or the like to create the body surface information, input information input by the user or the like to order the sheet such as personal information, and the like. Also, the communication unit 21 transmits information generated or computed by the sheet information generating unit 22, the input information analyzing unit 24, and the order information generating unit 28 to the information terminal P, the body surface information acquiring apparatus Q, or the sheet forming unit 300.

The sheet information generating unit 22 transmits information for acquiring the body surface information of the user such as counselling information for the user to input skin issues and the like to the information terminal P or the body surface information acquiring apparatus Q according to the access information received by the communication unit 21. For example, selection operation screen information as shown in FIG. 4(*a*) and adjustment operation screen information as shown in FIG. 4(*b*) are transmitted to the information terminal P or the body surface information acquiring apparatus Q via the communication unit 21. Also, the sheet information generating unit 22 transmits information for acquiring sheet information in which the shape and dimensions of the sheet are set for the individual user such as candidate sheet information. In the present embodiment, the sheet information generating unit 22 transmits each of the selection operation screen information and the adjustment operation screen information to the information terminal P in response to an operation request signal transmitted from the input information analyzing unit 24.

The input information analyzing unit 24 computes the type, shape or dimensions of the sheet 10 based on the body surface information of the user. The input information analyzing unit 24 of the present embodiment includes a counselling information analyzing unit 241 and a sheet size computing unit 245, and these units perform the computation described above. Specifically, the counselling information analyzing unit 241 performs, based on information regarding the counselling result of the user, computation processing for selecting one or more appropriate candidate sheets from among a plurality of types of sheets. For example, if the user inputs information indicating "pores on cheeks are noticeable" into the information terminal P, the counselling information analyzing unit 241 performs, based on the input information, computation processing for selecting a sheet(s) with light transmission for concealing the pores from among a plurality of types of sheets (sheet products) stored in the storage unit D1. Also, the counselling information analyzing unit 241 performs computation processing for selecting a sheet(s) that has a shape suitable for application to the cheek. Furthermore, the counselling information analyzing unit 241 narrows down the results of the computation processing to sheets that "conceal pores" and "have a shape suitable for application to the cheek" as candidate sheets. In this way, the counselling information analyzing unit 241 extracts, based on the information regarding the counselling result of the user, candidate sheet information regarding sheets with a predetermined shape and predetermined functions and properties (hereinafter referred to as "properties and the like"), and transmits the extracted information to the sheet information generating unit 22. The sheet information generating unit 22 transmits, to the information terminal P, information regarding a selection operation screen on which the candidate sheet information is displayed for the user to determine the sheet type. The user operates the selection operation screen, performs a terminal operation to select a sheet to be applied from among the candidate sheets, and determines the shape and the properties and the like of the sheet to be applied. Information regarding the shape and the properties and the like of the sheet that have been determined is transmitted to the sheet size computing unit 245, and also transmitted to the order information generating unit 28.

The sheet size computing unit 245 acquires body surface information so as to determine the application position and the size of the sheet whose shape and properties and the like have been determined, and computes the dimensions of the sheet based on the acquired information. For example, the sheet size computing unit 245 transmits a request for body surface information to the information terminal P or the body surface information acquiring apparatus Q. In the present embodiment, as the body surface information, image data of a part to which the sheet is to be applied is requested. The image data is acquired using the image capturing function of the information terminal P or the body surface information acquiring apparatus Q. The acquired body surface information such as image data is transmitted to the sheet size computing unit 245.

The sheet size computing unit 245 recognizes, based on the body surface information, the part to which the sheet is to be applied, and prompts the user to determine the application position and the size of the sheet whose shape and properties and the like have been determined. The sheet size computing unit 245 of the present embodiment, first, recognizes, in the image data, the part to which the sheet is to be applied, and then transmits a request to the sheet information generating unit 22 to perform an adjustment operation of adjusting the application position and the size of the sheet in the image data. The sheet information generating unit 22 receives an operation request signal regarding the request from the sheet size computing unit 245, and transmits information regarding an adjustment operation screen to the information terminal P or the body surface information acquiring apparatus Q. The user operates the adjustment operation screen and determines the application position of the sheet and the size of the sheet at the application position in the image data (see FIGS. 5(*a*) and 5(*b*)). Information regarding the sheet size in the image that has been determined is transmitted to the sheet size computing unit 245. The sheet size computing unit 245 performs, based on the information regarding the sheet size in the image, computation processing for computing the dimensions of the sheet. As the processing method, any method with which the actual size of the face of the user U and the dimensions of the sheet can be derived from an image can be employed without limitation. Specifically, a known method may be used such as a method in which a patch seal with predetermined dimensions is used as a scale and captured together with the part to which the sheet is to be applied, and the dimensions of the sheet are calculated based on the scale, a method in which the dimensions of the sheet are calculated by estimating the dimensions of a part of the face of the user U (the size of the eye or mouth of the user U, the length of an eyebrow of the user U, or the like) in an image based on the average size of that part of a human (the average size of the human eye or mouth, the average length of a human eyebrow, or the like), or a method in which the dimensions of the sheet are calculated based on geometric information (for example, epipolar geometry) obtained from images captured by a plurality of cameras. The part of the face of the user U in the image can be recognized or extracted based on image data (for example, color information based on pixels and the like in the image data). Information regarding the result of computation processing is stored in the storage unit D1, and also transmitted to the order information generating unit 28.

The input information analyzing unit 24 may also compute the type, shape or dimensions of the sheet 10 using a method other than the above-described processing methods. This will be described in greater detail by taking an example in which a "sheet model", a plurality of "face models", and a "shape database" for each sheet are stored in the storage unit D1 of the sheet specification determining unit 200, and the input information analyzing unit 24 has a "renderer" as a function thereof.

A "sheet model" refers to a model that represents the shape of the sheet in a simplified manner, and the dimensions of the sheet model are changed according to the operation performed by the user U. Initial values of the shape of the sheet model are any of the values that have been set in the shape database as will be described later. The sheet model can be changed to any desired shape afterward, and various parameters for changing the shape are set. That is, the shape of the sheet model can be changed by changing a parameter.

A "face model" refers to three-dimensional shape information that indicates a standard shape of the face of a human. A plurality of face models is prepared for different races, different genders, and different age groups, and a face model is selected as appropriate according to the attributes of a user. The shape information of the face models also includes information regarding various parts of the face. For example, three-dimensional coordinate values of the eyes, nose, mouth, and ears of each face model are set in the shape information. Note that, in the following description, the eyes, nose, mouth, and ears will be collectively referred to as "face parts".

The "renderer" refers to software with which an image, or in other words, a rendered image can be obtained by arranging a plurality of models and a light source in an imaginary three-dimensional space and observing the model from a suitable viewing position. The renderer is also called "rendering software", a "rendering engine", or the like. The renderer has the function of arranging, along the surface of the model, an additional model. For example, it is possible to arrange a sheet model on a suitable surface of a face model and render only the sheet model from a suitable viewing point. Thus, an image obtained by rendering the sheet model can be superimposed and displayed, or in other words, displayed overlaid on top of a face image F, thereby making it possible to confirm a state in which a product sheet is actually applied to the face.

The "shape database" refers to a database that indicates the relationship between an application position of the sheet on the face and a shape of the sheet, and application positions (parts to which the sheet are to be applied) on the face and shapes suitable for the respective application positions are recorded in the shape database in association with each other. The application positions are expressed as, for example, ranges defined by three-dimensional coordinates of corresponding regions on a face model. A shape of the sheet stored in the shape database is a three-dimensional shape of the sheet that has been set as an initial value, and a plurality of shapes has been set in advance.

Table 1 below is an example of the shape database. As described above, in the shape database, the correspondence between the application positions of the sheet and the shapes of the sheet is specified. All the information shown in Table 1 is conceptual. The "lower eyelid" shown in Table 1 is actually a specific range that is defined by three-dimensional coordinates and indicates a region below an eye of the face model. Also, the "bean shape" shown in Table 1 is actually a shape parameter of a specific three-dimensional sheet model with a shape such as that shown in FIG. 1.

In Table 1 below, certain portions of a list of application positions and sheet shapes that correspond to the application positions are omitted and shown in a simplified manner as " . . . ".

TABLE 1

| Application Position | Sheet Shape |
|---|---|
| Lower Eyelid | Bean Shape |
| Cheek | Circular Shape |
| Upper Portion of Nose | Horizontally-Long Rectangular Shape |
| Between Nose and Upper Lip | Horizontally-Long Rectangular Shape |
| . . . | . . . |

The processing that is performed in the case where the input information analyzing unit 24 has the above-described renderer will be described later using flowcharts shown in FIGS. 9 and 10.

In the step of optimizing the shape and the dimensions of the sheet through machine learning, the information utilization unit 26 performs processing for the machine learning. For the machine learning, learning data stored in the sheet specification determining unit 200 is used. Specifically, the information utilization unit 26 generates, from the access information stored in the communication unit 21, a machine learning model for optimizing the computation processing performed by the input information analyzing unit 24, and updates the program for the computation processing performed by the input information analyzing unit 24 through machine learning. The information utilization unit 26 of the present embodiment includes a feature component extracting unit 261 and a learning result judging unit 263, and performs machine learning by using these units. The feature component extracting unit 261 extracts features required for the machine learning from the access information stored in the storage unit D1 as well as order information and ordered sheet information that are stored in the customer information storage unit D3, which will be described later. The feature component extracting unit 261 may use main component analysis or a machine learning algorithm such as a neural network so as to extract information that serves as an indicator to perform machine learning. The learning result judging unit 263 performs suitable machine learning based on the information extracted by the feature component extracting unit 261, constructs a machine learning model based on the extracted information, and reflects the machine learning model in the computation processing performed by the input information analyzing unit 24. For example, the feature component extracting unit 261 goes back through counselling information of a plurality of users of a predetermined preceding period, and classifies skin issues into categories (for example, dryness, pores, wrinkles, skin dullness, and the like), and then extracts information regarding the frequency of each category and the sheet type ordered by the user. The learning result judging unit 263 learns the sheet type ordered under each category based on a correlation between the frequency and the ordered sheet type, using a machine learning algorithm such as a linear support vector machine (linear SVM) or a k-nearest neighbor algorithm, and reflects this in parameters, coefficients, and the like that are used in the computation processing performed by the input information analyzing unit 24. In the present embodiment, the database generated by the feature component extracting unit 261 and the machine learning model generated using the machine learning algorithm are stored in the learning data storage unit D2.

The order information generating unit 28 generates, based on the result of computation processing performed by the input information analyzing unit 24, information regarding the sheet whose shape and dimensions have been determined (hereinafter also referred to as "ordered sheet information") and order screen information, for each individual user. The ordered sheet information is information regarding the type, shape, and dimensions of the sheet that have been determined as described above, the identification number (product number) of the sheet, and the like. The order screen information is information regarding an order screen for the user to order a sheet. The order screen is displayed on the display unit of the information terminal P or the body surface information acquiring apparatus Q. The order screen is an operation screen for the user or the like to input order information such as the delivery destination of the sheet, desired delivery date, and the quantity of sheets. The order screen information generated by the order information generating unit 28 is transmitted to the information terminal P or the body surface information acquiring apparatus Q via the communication unit 21.

Figure 7:
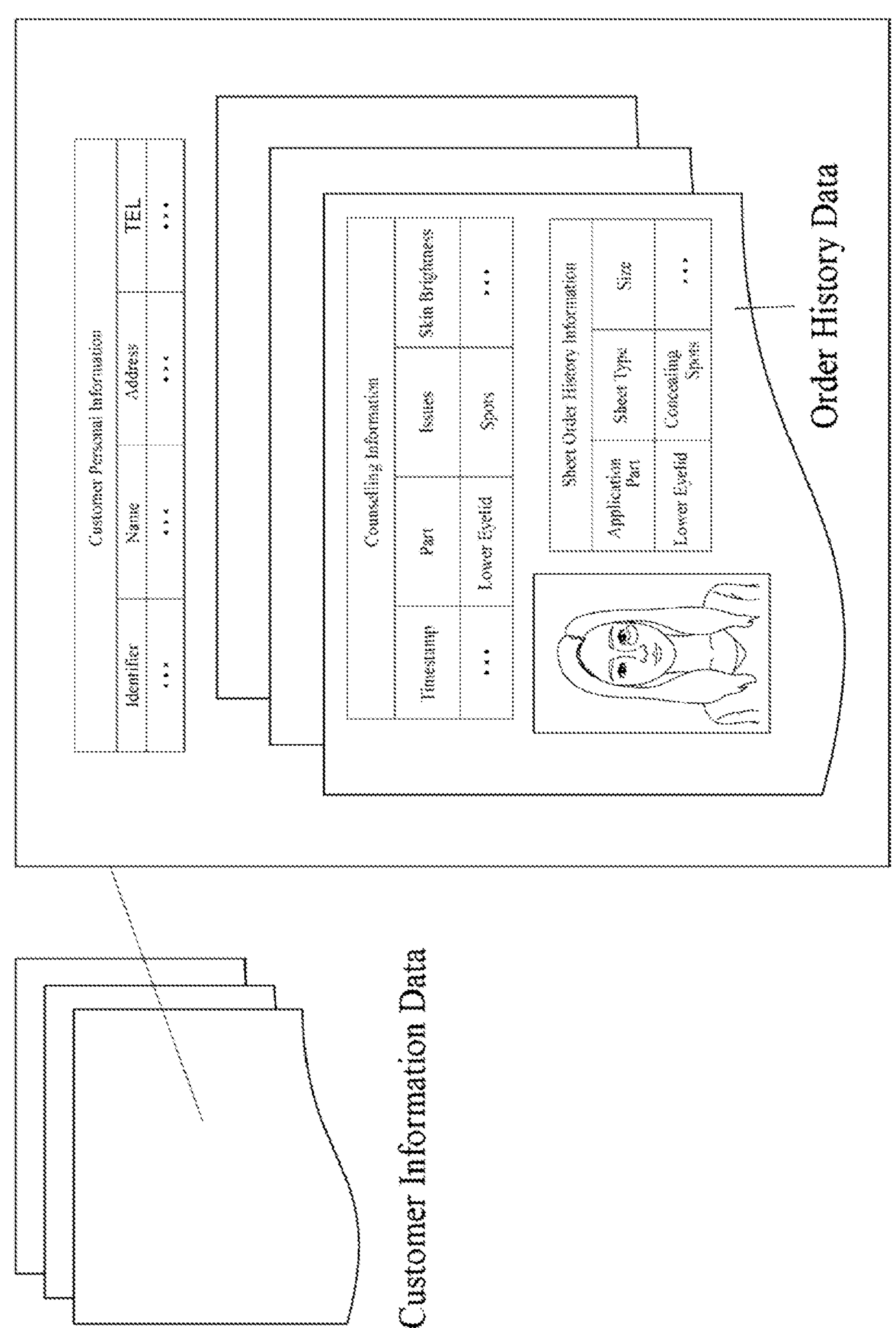
FIG. 7 is an illustrative diagram showing an example of data stored in a storage unit shown in FIG. 6.

Also, the order information generating unit 28 generates customer information data in which, for each individual user, order history data of order information that has been input by the user or the like is collected, and stores the customer information data in the customer information storage unit D3, and also transmits the order information and the ordered sheet information to the sheet forming unit 300 via the communication unit 21. In the customer information storage unit D3, for example, as shown in FIG. 7, order history data is stored for each individual user, the order history data being data in which personal information including the name, address, and the like of the user and order history data including a sheet(s) ordered by the user in the past, counselling information used to order the sheet(s), the application position(s) of the sheet(s), and the like are associated. The ordered sheet information transmitted to the sheet forming unit 300 is information regarding the sheet shape and dimensions that have been determined as described above, the product number for identifying the sheet that has the sheet shape and dimensions, and the like. The order information transmitted to the sheet forming unit 300 is information regarding a sheet delivery destination to be printed on a package, the quantity of sheets ordered, and the like. The customer information data stored in the customer information storage unit D3 is used in the above-described machine learning.

The storage unit D1 stores various types of programs, data, parameters, and the like that are required for the sheet specification determining unit 200 to perform computation and processing under control of each of the communication unit 21, the sheet information generating unit 22, the input information analyzing unit 24, the information utilization unit 26, and the order information generating unit 28. The storage unit D1 stores, in addition to the input information such as the access information and the order information described above, output information transmitted to the information terminal P, the body surface information acquiring apparatus Q, or the sheet forming unit 300 via the communication unit 21, and the like.

In each of the storage unit D1, the learning data storage unit D2, and the customer information storage unit D3, a database system or a file system may be used. Each of the storage unit D1, the learning data storage unit D2, and the customer information storage unit D3 includes, for example, a main storage device that includes a ROM and a RAM, an auxiliary storage device composed of a non-volatile memory and the like, and various types of recording media such as an HDD (Hard Disk Drive), an SSD (Solid State Drive), and a flash memory.

Here, as the sheet specification determining unit 200, a sheet specification determining unit that includes the communication unit 21, the sheet information generating unit 22, the input information analyzing unit 24, the information utilization unit 26, the order information generating unit 28, the storage unit D1, the learning data storage unit D2, and the customer information storage unit D3 is described; however, the sheet specification determining unit 200 does not need to include all of these components, and as long as it includes the communication unit 21, the sheet information generating unit 22, and the input information analyzing unit 24, the information acquiring step (A1) of acquiring the body surface information of individual users and the shape and dimension determining step (A2) of determining a shape and dimensions of the sheet 10 for each individual user based on the body surface information can be carried out.

The sheet forming unit 300 comprises, in addition to the sheet layer forming apparatus 40, the cutting apparatus 50, and the handling apparatus 60 that were described above, a communication unit 31, a production data deriving unit 33, a production control unit 35, and an information assigning unit 37.

The communication unit 31 receives the order information and the ordered sheet information transmitted from the sheet specification determining unit 200 via the network N.

The production data deriving unit 33 derives production information for producing the sheet based on the information regarding the shape and the dimensions of the sheet included in the ordered sheet information received by the communication unit 31. The production information for producing the sheet is control information for controlling the sheet layer forming apparatus 40, the cutting apparatus 50, and the handling apparatus 60 based on the shape and the dimensions of the sheet. In the present embodiment, the production information is information regarding control of movement of the discharge nozzle 41, control of the discharge amount of the raw material, and control of cutting of the sheet to have a desired shape.

The information regarding control of movement of the discharge nozzle 41 includes, for example, information that indicates the movement trajectory of the discharge nozzle 41 in a coordinate system composed of the X axis and the Y axis, information regarding the moving speed of the discharge nozzle 41 (the factor a), information regarding the distance between the discharge nozzle 41 and the continuous sheet 12*a* of the base layer (the factor c), and the like. The information that indicates the movement trajectory of the discharge nozzle 41 is information that relates to "predetermined shape in plan view" of the sheet layer 11, and the outer edge portion of the movement trajectory is reflected in the profile shape of the sheet layer 11.

The information regarding control of the discharge amount of the raw material is, for example, the discharge amount of the raw material set at each position in the coordinate system composed of the X axis and the Y axis. The discharge amount is the discharge amount per unit area or the discharge amount per unit time (the factor b).

The information regarding control of cutting is, for example, information that indicates the movement trajectory of laser processing.

The information regarding control of movement of the discharge nozzle 41 and the information regarding control of the discharge amount of the raw material are obtained by simulating, based on the information regarding the shape and the dimensions of the sheet, a movement trajectory that has a predetermined shape in plan view and satisfies a condition in which the thickness has a predetermined numerical value in the trajectory calculation step. That is, the production data deriving unit 33 carries out the above-described trajectory calculation step based on the information regarding the shape and the dimensions of the sheet, and derives the information regarding control of movement of the discharge nozzle 41 and the information regarding control of the discharge amount of the raw material.

Also, the production data deriving unit 33 derives information regarding control of cutting based on the information regarding the shape and the dimensions of the sheet. For example, the production data deriving unit 33 derives, based on the information regarding the shape and the dimensions of the sheet, a trajectory that is located at a position spaced apart from the profile (the circumferential edge 17) of the sheet layer 11 toward the outer side of the sheet layer 11 and extends along the profile of the sheet layer 11. By performing laser processing on the continuous sheet 12*a* of the base layer 12 along the trajectory, a base layer 12 that has a shape in plan view substantially similar to that of the sheet layer 11 can be cut out from the continuous sheet 12*a*.

The production control unit 35 controls the sheet layer forming apparatus 40, the cutting apparatus 50, and the handling apparatus 60 of the sheet forming unit 300 based on the production information derived by the production data deriving unit 33. The production control unit 35 of the present embodiment includes a nozzle movement control unit 351 that controls movement of the discharge nozzle 41 of the sheet layer forming apparatus 40, a raw material discharge amount control unit 353 that controls the discharge amount of the raw material from the discharge nozzle 41, a cut control unit 354 that controls the cutting apparatus 50, and a handling control unit 356 that controls the handling apparatus 60. The units included in the production control unit 35 control the sheet layer forming apparatus 40, the cutting apparatus 50, and the handling apparatus 60 based on the production information derived by the production data deriving unit 33.

The information assigning unit 37 assigns, to a sheet produced based on the order information received by the communication unit 31, identification information of the sheet. The identification information is information with which an individual sheet can be specified, such as an identifier or the production number of the sheet. The identification information may be indicated by, for example, characters, numbers, symbols or a combination thereof, or may be indicated in an electronically readable form. As the electronically readable form, for example, a two-dimensional code such as a barcode or a QR code (registered trademark), an electronic information medium such as an RFID (Radio Frequency Identification) tag, or the like is used. The RFID tag can be read using an RFID reader (RFID antenna). Also, the information assigning unit 37 assigns the order information such as delivery destination to the package in which the sheet is packed.

Figure 8:
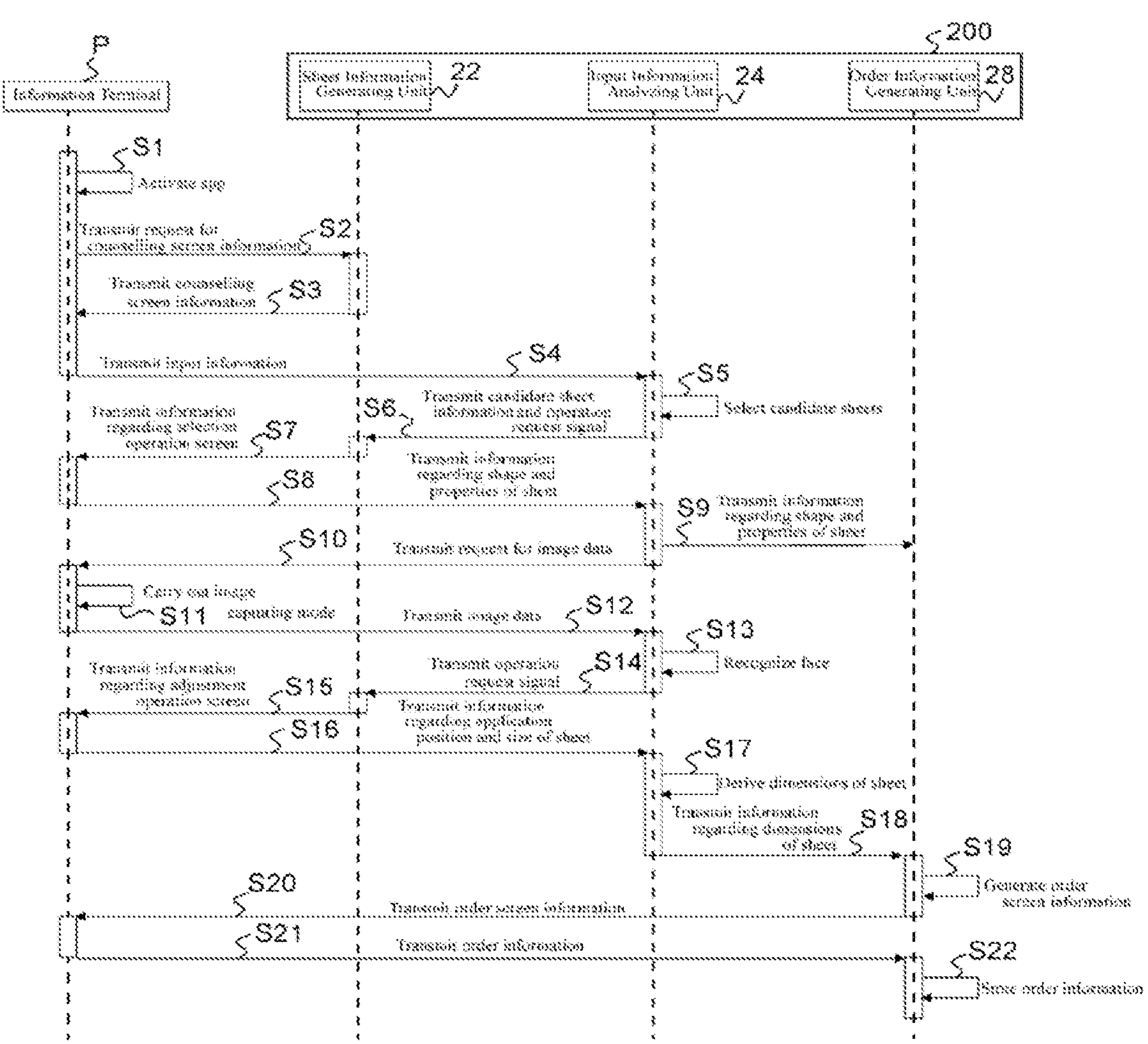
FIG. 8 is a sequence diagram showing an example of a determining step (A) carried out by the system shown in FIG. 6.

Next, processing performed by the system 100 of the present embodiment will be described, along with the determining step (A) and the forming step (B) of the sheet providing method of the embodiment described above. FIG. 8 shows a sequence diagram illustrating the processing performed by the system 100 in the determining step (A).

In the determining step (A), an information terminal P activates an app used by the system 100 (step S1), and transmits, to the sheet specification determining unit 200, a request for counselling screen information for displaying counselling information (step S2). The counselling screen information is information regarding an operation screen in a questionnaire form for the user to answer questions regarding skin issues and the like. Next, the sheet information generating unit 22 of the sheet specification determining unit 200 transmits the counselling screen information to the information terminal P (step S3) so as to cause an operation screen based on the screen information to be displayed on the display unit of the information terminal P. The user or the like performs an operation of inputting information regarding skin issues and the like based on the information displayed on the operation screen. The input information input via the operation is transmitted from the information terminal P to the input information analyzing unit 24 of the sheet specification determining unit 200 (step S4). Next, the input information analyzing unit 24 selects, based on the input information, one or more sheets that have an appropriate shape and appropriate properties and the like from among a plurality of types of sheets stored in the storage unit D1 (step S5), and transmits the selected sheets as candidate sheets to the sheet information generating unit 22 and also transmits an operation request signal for the user to select a sheet to be applied from among the candidate sheets (step S6). The processing in step S5 is performed by the counselling information analyzing unit 241 (not shown). Next, the sheet information generating unit 22 transmits, to the information terminal P, information regarding a selection operation screen for presenting candidate sheet information for the user to determine the sheet type (step S7). The user operates the selection operation screen and selects a sheet to be applied from among the candidate sheets (see FIG. 4(*a*)). Accordingly, the shape and the properties and the like of the sheet to be applied are determined. Information regarding the shape and the properties and the like of the sheet is transmitted to the input information analyzing unit 24 (step S8), and also transmitted to the order information generating unit 28 (step S9).

Next, the input information analyzing unit 24 transmits, to the information terminal P, a request for image data of a part to which the sheet is to be applied as body surface information (step S10). Accordingly, an image capturing mode is carried out in the information terminal P (step S11) The user captures an image of the part to which the sheet is to be applied such as the face using the information terminal P in the image capturing mode. The image data is transmitted from the information terminal P to the input information analyzing unit 24 of the sheet specification determining unit 200 (step S12). Accordingly, the body surface information is acquired. Next, the input information analyzing unit 24 recognizes, based on the transmitted image, the face as the part to which the sheet is to be applied (step S13). The processing in step S13 is performed by the sheet size computing unit 245 (not shown) of the input information analyzing unit 24. Next, the input information analyzing unit 24, specifically, the sheet size computing unit 245 transmits an operation request signal for adjusting the size of the sheet to the sheet information generating unit 22 (step S14). The sheet information generating unit 22 transmits, to the information terminal P, information regarding an adjustment operation screen for the user to determine the size of the sheet (step S15). The user operates the adjustment operation screen, and performs an operation of adjusting the application position of the sheet and the size of the sheet at the application position (see FIGS. 5(*a*) and 5(*b*)). Through the terminal operation, the application position and the size of the sheet on the image data are determined. Information regarding the application position and the size of the sheet is transmitted to the input information analyzing unit 24 (step S16), and the sheet size computing unit 245 (not shown) of the input information analyzing unit 24 derives the dimensions of the sheet based on the transmitted information (step S17). After that, information regarding the dimensions of the sheet is transmitted to the order information generating unit 28 (step S18).

The order information generating unit 28 generates information (ordered sheet information), for each individual user, regarding the sheet whose shape and dimensions have been determined based on the information regarding the properties and the like, shape, and dimensions of the sheet transmitted from the input information analyzing unit 24 (this step is not shown), and order screen information for the user to order the sheet (step S19), and transmits the order screen information to the information terminal P (step S20). Accordingly, an order screen for the user to order the sheet is displayed on the display unit of the information terminal P. The user inputs, on the order screen, order information such as the delivery destination and the desired delivery date of the sheet, and the quantity of sheets. The input order information is transmitted to the order information generating unit 28 (step S21), and the order information is stored in the customer information storage unit D3 (step S22). After step S22, information indicating that the order of the sheet is complete is displayed on the display unit of the information terminal P (this step is not shown). Also, the order information generating unit 28 transmits the order information and the ordered sheet information to the sheet forming unit 300 via the communication unit 21 (this step is not shown).

Next, processing that is performed by the information terminal P and the sheet specification determining unit 200 in the above-described steps S1 to S22 will be described using FIGS. 9 and 10, by taking an example in which the sheet specification determining unit 200 derives a sheet for concealing spots, based on the body surface information (an image of the skin) transmitted from the information terminal P.

Figure 9:
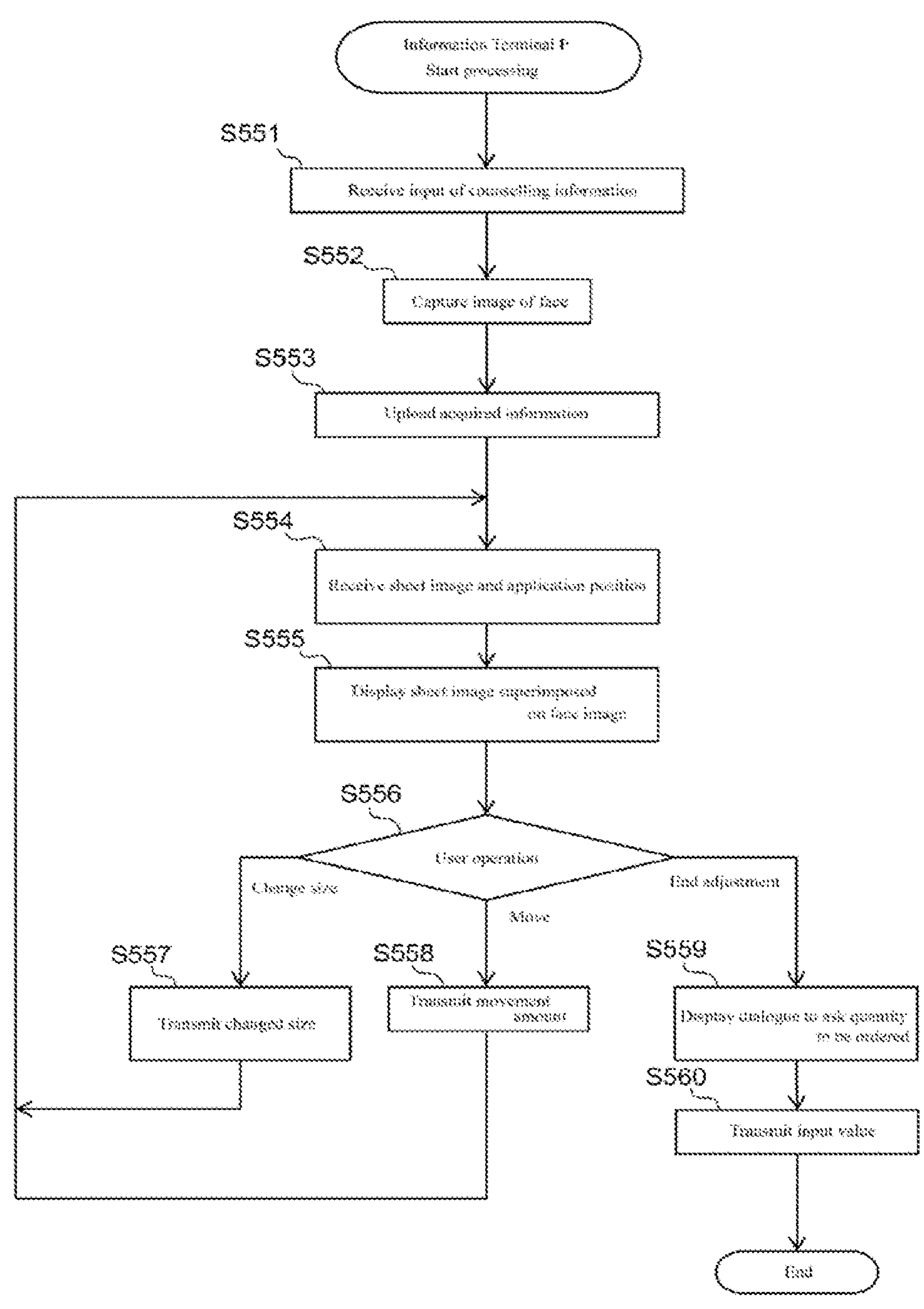
FIG. 9 is a flowchart showing an example of processing carried out by an information terminal P shown in FIG. 6 with respect to the determining step (A).

FIG. 9 shows a flowchart illustrating the processing performed by the information terminal P. Note that steps described below are carried out by the CPU of the information terminal P.

In step S551 shown in FIG. 9, input of the above-described counselling information is received. In the present embodiment, the counselling information includes, in addition to the above-described information regarding skin issues, information regarding the age, gender, and the like of the user U. The input of the counselling information may be performed by using a character input function of the OS of the information terminal P, or may be performed through voice input or gesture input.

In subsequent step S552, an image of the face of the user U is captured using a built-in camera of the information terminal P. Hereinafter, the image that is captured in step S552 will be referred to as "face image F". In subsequent step S553, the information acquired in steps S551 and S552 is uploaded to the sheet specification determining unit 200, and the procedure advances to step S554. The information uploaded in step S553 is the counselling information and the face image of the user U.

In step S554, a sheet image is received from the sheet specification determining unit 200. The sheet image is an image of a sheet derived by the sheet specification determining unit 200 based on the counselling information (see step S505, which will be described later). In subsequent step S555, with respect to the face image F acquired in the step S552, the sheet image received in step S554 is superimposed on the face image F and displayed on the display unit of the information terminal P. In subsequent step S556, a user interface is displayed to prompt the user U to make a selection, and an operation performed by the user U is judged. The user interface is an interface for the user to select any one of the following options: move the sheet; change the sheet size; and end the sheet adjustment (see FIGS. 4(*a*) and 4(*b*)). For example, if the user U performs an operation of dragging the sheet (sheet image) displayed on a touch panel, or operates a Move button displayed on the display unit, it can be judged that move the sheet has been selected. Also, if the user U performs an operation of pinching the sheet (sheet image) displayed on a touch panel, or operates a Zoom In and Zoom Out button displayed on the display unit, it can be judged that change the sheet size has been selected. Furthermore, if the user U operates an "End Adjustment" button displayed on the display unit, it can be judged that end the sheet adjustment has been selected. In step S556, if it is judged that the user U has selected change size, the procedure advances to step S557; if it is judged that the user U has selected move the sheet, the procedure advances to step S558; and if it is judged that the user U has selected end adjustment, the procedure advances to step S559.

In step S557, information regarding the changed size of the sheet whose size has been changed according to an operation performed by the user U is transmitted to the sheet specification determining unit 200, and the processing returns to step S554. The information regarding the changed size of the sheet is, for example, a numerical value that indicates the changed size of the sheet relative to the present size of the sheet that is taken as "100". If the size of the sheet is enlarged to 2 times the present size, "200" is transmitted, and if the size of the sheet is reduced to 0.75 times the present size, "75" is transmitted.

In step S558, information regarding the movement amount of the sheet that has been moved by the user U is transmitted to the sheet specification determining unit 200, and the processing returns to step S554. The movement amount is the amount of movement in the X direction and the Y direction on a two-dimensional plane displayed on the display unit.

In step S559, a dialogue that asks the quantity of sheets to be ordered is displayed on the display unit. In subsequent step S560, an input from the user U is transmitted to the sheet specification determining unit 200, and the processing illustrated in FIG. 9 ends.

Figure 10:
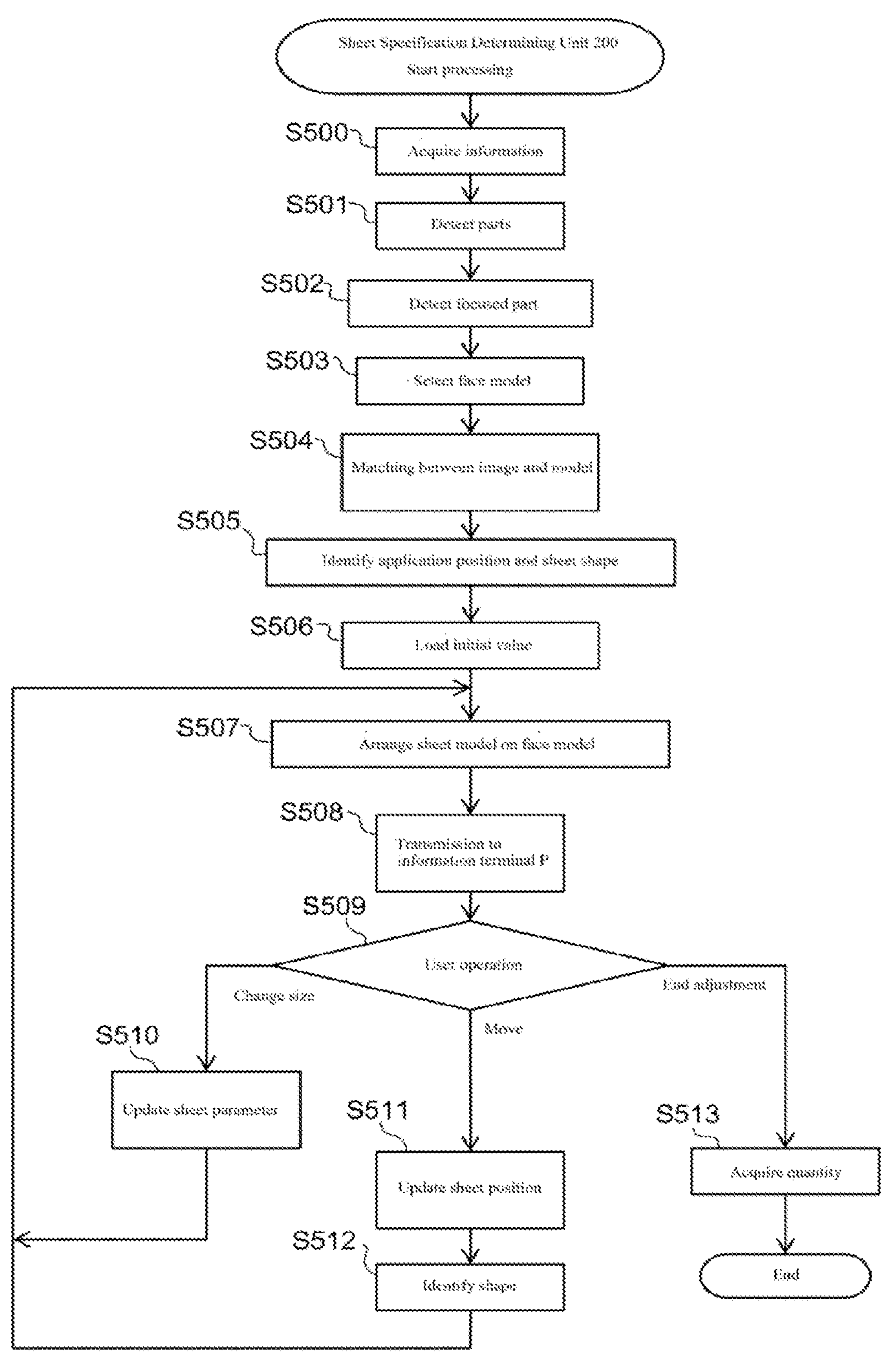
FIG. 10 is a flowchart showing an example of processing carried out by a sheet specification determining unit 200 shown in FIG. 6 with respect to the determining step (A).

FIG. 10 shows a flowchart that corresponds to FIG. 9 and illustrates the processing performed by the sheet specification determining unit 200. Note that steps described below are carried out by the CPU of the sheet specification determining unit 200. When the information is uploaded in step S553 of FIG. 9, the processing shown in FIG. 10 is started.

In step S500, the information uploaded by the information terminal P is acquired. In the present step, the counselling information including the age and the gender of the user U as well as the face image F are acquired. In subsequent step S501, the face parts are detected from the face image F that is used as the target of processing. Specifically, the eyes, nose, mouth, and ears in the face image F are detected through pattern matching, or using a cascade classifier that has performed learning in advance, and coordinates of the detected face parts on the face image F are identified.

In subsequent step S502, a part (hereinafter referred to as "focused part") that is designated by the user U as a part where there are skin issues is detected from the face image F based on the counselling information. In order to perform the detection, the input information analyzing unit 24 judges, based on the counselling information that is input by the user U in step S551, which category the focused part is to be classified into, from among categories such as spots, wrinkles, skin elasticity, and the like (this step is not shown in FIG. 10). A database that indicates the relationship between focused parts and the categories is stored in the storage unit D1 of the sheet specification determining unit 200 in advance, and which category the focused part belongs to is judged based on the database and the counselling information input by the user U in step S551. For example, which category (spots, wrinkles, skin elasticity, or the like) the focused part belongs to is judged based on matching between the input counselling information and text relating to a category. Then, the focused part in the face image F is detected. A processing method for performing the detection will be described taking an example in which the focused part is "spots". First, a face region is extracted from the face image F, and an average skin color of the user U is obtained by calculating an average of colors of the face region excluding certain parts such as the hair, eyes, mouth, eyebrows, and the like. Next, for each pixel in the face region of the face image F, a difference (color difference) between the pixel and the calculated average skin color is calculated. Then, information regarding the thus obtained color difference is binarized, and a point cloud generated as a result of the binarization processing is divided into groups. Furthermore, the groups are classified into "spots" and "wrinkles" based on the magnitude of the variance of the point cloud in each group. Specifically, a group in which the value of the variance is equal to or greater than a predetermined threshold value is classified as "spots", and a group in which the value of the variance is less than the predetermined threshold value is classified as "wrinkles". Then, a group of the point cloud that matches the category of the focused part is selected. That is, in the case where the focused part is "spots", a group classified as "spots" is selected, and the center coordinates and the coordinate region of points of the point cloud that are classified into the selected group in the face image F are calculated. The number of spots and the number of wrinkles for which the calculation in step S502 is performed is not limited to 1, and the calculation may be performed for a plurality of spots and a plurality of wrinkles.

In subsequent step S503, based on the gender and the age of the user U included in the counselling information acquired in step S500, an optimum face model is selected from a plurality of face models prepared in advance.

In subsequent step S504, matching between the face model selected in step S503 and the face image F is performed. The coordinates of the face parts in the face image F were identified in step S501, and are therefore compared with three-dimensional coordinates of corresponding face parts that have been set in advance in the face model.

In subsequent step S505, the position of a spot in the face model that was calculated in step S502 is identified using the result of the matching in the step immediately before step S505, and a sheet model (a sheet shape) is identified by referring to the shape database stored in the storage unit D1. Specifically, since the center coordinates of individual face parts in the face image F have been identified so as to correspond to the coordinates in the face model, the coordinates of the spot in the face image F that were calculated in step S502 can be converted into coordinates in the face model using a method such as proportional interpolation. Then, the coordinates in the face model that are obtained as a result of the conversion are checked against the shape database, and thus, initial parameters of the sheet model are identified. Accordingly, the application position of the sheet in the face image F and the shape of the sheet to be applied are identified. Note that the processing in the present step is repeated the same number of times as the number of spots detected in step S502.

In subsequent step S506, the renderer of the input information analyzing unit 24 is activated, and the sheet model is newly created in a three-dimensional space managed by the renderer, and the initial parameters identified in step S505 are loaded into the sheet model (initial value loading). That is, the initial parameters are reflected in the sheet model. Note that, in the case where a plurality of spots is detected in step S502, the same number of sheet models as the number of detected spots are created, and initial parameters corresponding to the individual spots are loaded. At this time, the parameters may be adjusted so as to change the size of each of the sheet models to the minimum size that covers the entire region of the corresponding spot. Since the region in which the spot is present in the face image F has been calculated in step S502, a region in which the spot is present in the face model can also be calculated using a method similar to the method with which the three-dimensional coordinates corresponding to the center coordinates are identified in the face model.

In subsequent step S507, the face model identified in step S503 is loaded into a three-dimensional space managed by the renderer, and the center of the sheet model is arranged at the position calculated in step S505. At this time, the renderer changes the shape of the sheet model following the surface of the face model. In this manner, in step S507, a rendered image is acquired by performing rendering of the sheet model using the renderer. Furthermore, the coordinates of the sheet model in the same three-dimensional space as the face model are converted into coordinates in the face image F by performing the processing of step S505 in reverse order (this step is not shown in FIG. 10).

In subsequent step S508, the rendered image and the coordinate values obtained in step S507 are transmitted to the information terminal P. Note that the information transmitted in the present step is received in step S554 of FIG. 9.

In subsequent step S509, the operation performed by the user U and transmitted from the information terminal P in step S556 is judged. If the operation performed by the user U is judged as an operation to change the size, the procedure advances to step S510; if it is judged as an operation to move the sheet, the procedure advances to step S511; and if it is judged as an operation to end the sheet adjustment, the procedure advances to step S513. For example, if the information regarding the changed size of the sheet is received, the operation performed by the user U is judged as an operation to change the size; if the information regarding the movement amount of the sheet is received, the operation performed by the user U is judged as an operation to move the sheet; and if information to the effect that the End Adjustment button has been pressed is received, the operation performed by the user U is judged as an operation to end the adjustment.

In step S510, parameters of the sheet model are updated based on the information regarding the changed size of the sheet, the information being received from the information terminal P, and the processing returns to step S507. For example, if "200" is received from the information terminal P in step S557 as a numerical value that indicates the changed sheet size, the parameters are updated such that the dimensions of the sheet model are increased to 2 times the present dimensions of the sheet.

In step S511, coordinate values obtained by adding the movement amount received from the information terminal P to the coordinate values calculated in step S507 are converted into coordinates in the face model to thereby update the position of the sheet model. The processing in step S511 is performed in a similar manner to the processing in step S505. In subsequent step S512, the shape of the sheet model whose position was updated in step S511 is identified by referring to the shape database, parameters are set, and the processing returns to step S507.

In step S513, the input value of the quantity of sheets ordered transmitted from the information terminal P in step S560 is received, and the processing illustrated in FIG. 10 ends.

In the position and size determining step (A2-2) in which the above-described processing illustrated in FIGS. 9 and 10 is performed, the information regarding the dimensions of the sheet is updated in real time according to the operation performed on the adjustment operation screen by the user U, and the updated information is displayed on the adjustment operation screen. Also, the application position of the sheet and the size of the sheet are identified based on information (coordinates) regarding the position of a discolored portion such as a spot in the face image F (steps S502 to S513), and therefore, operations such as dragging performed by the user U to determine the application position and the size of the sheet can be simplified. In this manner, it is also possible to display information regarding a candidate position of the application position of the sheet (hereinafter also referred to as "candidate position information") on the adjustment operation screen, and prompt the user U to determine whether or not to choose the position indicated by the candidate position information as the application position of the sheet. As in step S502, the candidate position information is generated based on information regarding the position of a discolored portion such as a spot on the skin on the adjustment operation screen (the above-described information regarding the coordinates of the point cloud).

Figure 11:
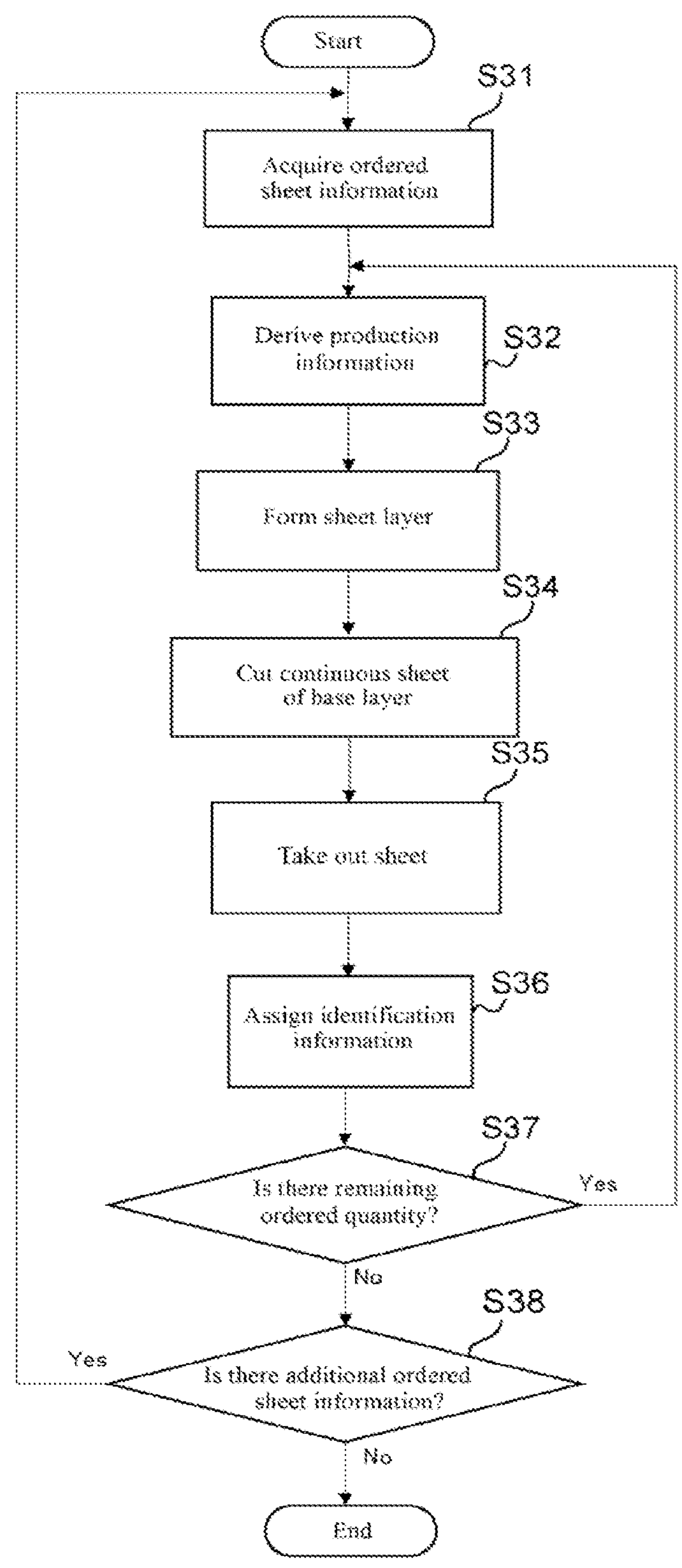
FIG. 11 is a flowchart showing an example of a forming step (B) carried out by the system shown in FIG. 6.

FIG. 11 shows a flow diagram illustrating the processing performed by the system 100 in the forming step (B).

In the forming step (B), first, ordered sheet information is transmitted from the sheet specification determining unit 200 to the sheet forming unit 300. Accordingly, the sheet forming unit 300 acquires the ordered sheet information (step S31). Next, the production data deriving unit 33 of the sheet forming unit 300 derives production information for producing the sheet from the ordered sheet information based on the information regarding the shape and the dimensions of the sheet (step S32). The production information is transmitted to the production control unit 35, and the nozzle movement control unit 351 and the raw material discharge amount control unit 353 control the discharge nozzle 41 based on the production information, and thereby a sheet layer 11 is formed (step S33). When the sheet layer 11 has been formed in step S33, the cut control unit 354 controls the cutting apparatus 50 based on the production information so as to cut the continuous sheet 12*a* of the base layer (step S34), and furthermore, the handling control unit 356 controls the handling apparatus 60 based on the production information so as to take out the produced sheet (step S35). The information assigning unit 37 assigns identification information to the thus obtained sheet based on the order information and the ordered sheet information (step S36). Next, the sheet forming unit 300 judges, for the sheet produced through the processing in steps S31 to S36, whether or not there is a remaining ordered quantity based on the ordered sheet information (step S37). If it is determined in step S37 that there is a remaining ordered quantity, the procedure returns to step S32, and the processing in step 32 and the subsequent steps is repeated. If it is determined in step S37 that there is no remaining ordered quantity, the procedure advances to step S38. Next, the sheet forming unit 300 judges whether or not there is additional ordered sheet information (step S38). If it is determined in step S38 that there is additional ordered sheet information, the procedure returns to step S31, and the processing in step 31 and the subsequent steps is repeated. If it is determined in step S38 that there is no additional ordered sheet information, the processing in the forming step (B) ends. The sheets produced in the manner described above are packed in a package, and the order information such as the delivery destination is assigned to the package by the information assigning unit 37. The package is delivered to the user based on the delivery destination.

Up to here, the present invention has been described by way of a preferred embodiment thereof, but the present invention is not limited to the embodiment given above, and may be changed as appropriate.

For example, the providing method of the embodiment described above is configured to provide, to a user, a cosmetic sheet to be applied to the face for cosmetic purposes such as skin care and makeup, but the purpose of the sheet is not limited to cosmetic purposes. For example, the providing method may be configured to provide a sheet that is to be applied to the body surface and on which a design or the like has been printed. Specifically, by applying a sheet on which a design or the like has been printed to the body surface, a finish similar to that obtained in the case where the design is drawn directly on the body surface can be obtained. In the case where an elaborate design is used, the sheet providing method that is configured as described above can provide excellent working efficiency as compared with the case where the design is drawn directly on the body surface. Also, examples of the sheet on which a design or the like has been printed include a colored sheet that has been colored in the same color as, or a similar color to, the skin color of the user U by performing printing, a printed sheet on which an image that imitates a feature on skin, such as moles, pimples, wounds, and wrinkles, has been printed, and the like. The color of the colored sheet is determined based on the information regarding the skin color.

Also, the providing method of the embodiment described above is configured to provide, to a user, a sheet to be applied to the face, but the body part to which the sheet can be applied is not limited to the face, and may be any of the body parts listed in the examples of the body part to which the sheet is to be applied.

Also, the sheet providing method of the embodiment described above comprises a step of optimizing the shape and the dimensions of the sheet determined in the determination processing step (A2-3) through machine learning. However, the sheet providing method according to the present invention does not necessarily include the step of optimizing the shape and the dimensions of the sheet through machine learning. Likewise, the sheet providing system according to the present invention does not necessarily comprise the information utilization unit 26 and the learning data storage unit D2.

Also, in the sheet providing method of the embodiment described above, in the shape selecting step (A2-1), the information indicating the functions and properties of the sheet is presented together with the shape of the sheet for the user to determine the sheet shape. However, only information regarding the shape of the sheet may be presented for the user to determine the sheet shape. In this case, the counselling information analyzing unit 241 extracts, based on information regarding the counselling result of the user, candidate sheet information regarding candidate sheets with a predetermined shape, and transmits the extracted information to the sheet information generating unit 22.

The sheet providing method of the embodiment described above is performed using the system 100 that includes the sheet specification determining unit 200 and the sheet forming unit 300. However, the sheet providing method may also be performed using a system that has a form different from the system 100. For example, the sheet providing method may be performed using a system that includes a sheet specification determining unit 200 and a sheet formation instructing unit that generates control instruction information for controlling a discharge nozzle that discharges a raw material of the sheet, and thereby forms the sheet. The sheet formation instructing unit includes a communication unit and an instruction information deriving unit that derives the control instruction information, and is constituted by a general-purpose computer that is separate from the sheet forming unit 300 and the sheet specification determining unit 200. The communication unit included in the sheet formation instructing unit receives order information and ordered sheet information transmitted from the sheet specification determining unit 200, via a network N. Also, the communication unit transmits the control instruction information derived by the instruction information deriving unit to the sheet forming unit 300 via the network N. The control instruction information is synonymous with the above-described production information derived by the production data deriving unit 33. The instruction information deriving unit has a similar configuration to that of the production data deriving unit 33 described above, and derives the control instruction information based on the information regarding the shape and the dimensions of the sheet included in the ordered sheet information received by the communication unit. After receiving the control instruction information, the sheet forming unit 300 controls the sheet layer forming apparatus 40, the cutting apparatus 50, or the handling apparatus 60 based on the received control instruction information, thereby forming the sheet.

Also, in addition to the above-described forms, a system in which the sheet specification determining unit 200 comprises the instruction information deriving unit described above may also be used. In this case, the sheet specification determining unit 200 includes a communication unit 21, a sheet information generating unit 22, and an input information analyzing unit 24, as well as the instruction information deriving unit.

Also, the functions that have been described in the description of the embodiment above may be realized by hardware, software, or firmware, or a suitable combination thereof. When the functions are realized by software, the functions may also be stored on a computer-readable storage medium or recording medium, as one or more instructions or codes of a program. The computer-readable storage medium or recording medium may be any usable medium that can be accessed by a general-purpose or dedicated computer. As a non-limiting example, such a computer-readable storage medium or recording medium can be used to store a desired program code means in the form of a RAM, a ROM, an EEPROM, a CD-ROM, or other optical disk storages; magnetic disk storages or other magnetic storage devices; or instructions or data structures, and can include any other media that can be accessed by a general-purpose or dedicated computer, or a general-purpose or dedicated processor.

With respect to the embodiment described above, the present invention further discloses a sheet providing method and a sheet providing system described below.

INDUSTRIAL APPLICABILITY

According to the present invention, it is possible to provide a sheet that reflects the wishes of a user.

The invention claimed is:

1. A method for producing a sheet configured to be applied to a body surface of an individual user, the method comprising:

(A) determining, using a sheet specification determining unit, a shape and dimensions of a sheet for an individual user based on body surface information of the individual user; and (B) forming, using a sheet forming unit that includes a discharge nozzle, the sheet by discharging a raw material of the sheet through the discharge nozzle to form a sheet having the shape and the dimensions of the sheet for the individual user, wherein the determining (A) comprises:

(A1) acquiring the body surface information of the individual user; and (A2) determining the shape and the dimensions of the sheet for the individual user based on the acquired body surface information by:

(A2-1) prompting a user to select a sheet shape; and (A2-2) prompting the user to determine an application position of the sheet and a size of the sheet, and wherein the shape and the dimensions of the sheet suited to the user are determined based on the body surface information, the sheet shape selected by the user, and information regarding the application position of the sheet and the size of the sheet determined by the user.

2. The sheet providing method according to claim 1, wherein the body surface information is acquired using an information terminal, or an apparatus capable of acquiring the body surface information.

3. The sheet providing method according to claim 1, wherein, in the forming (B), the sheet is formed by moving the discharge nozzle along a trajectory based on the information regarding the shape and the dimensions of the sheet while discharging the raw material from the discharge nozzle.

4. The sheet providing method according to claim 3, wherein the forming includes controlling at least one selected from the group consisting of a discharge amount of the raw material, a discharge position of the raw material, and the movement trajectory of the discharge nozzle, so as to achieve the shape and the dimensions of the sheet.

5. The sheet providing method according to claim 1, wherein the sheet comprises a base layer and a sheet layer that is made of the raw material.

6. The sheet providing method according claim 1, wherein the sheet is made of fibers formed from the raw material, and the fibers have a fiber diameter of 0.1 μm or more and 6.0 μm or less.

7. The sheet providing method according to claim 1, wherein the determining (A) comprises:

transmitting the body surface information of the individual user to the sheet specification determining unit via a network, and wherein the forming (B) comprises:

transmitting the information regarding the shape and the dimensions of the sheet to the sheet forming unit via a network; and moving the discharge nozzle along a trajectory that is set based on the information regarding the shape and the dimensions of the sheet while discharging the raw material from the discharge nozzle.

8. A system for producing a sheet configured to be applied to a body surface of an individual user, the system comprising:

a sheet specification determining unit configured to determine a shape and dimensions of a sheet for an individual user based on body surface information of the individual user; and a sheet forming unit that includes a discharge nozzle configured to form the sheet by discharging a raw material of the sheet through the discharge nozzle to form a sheet having the shape and the dimensions of the sheet for the individual user;

and a sheet formation instructing unit configured to generate control instruction information for controlling the discharge nozzle of the sheet forming unit, wherein the sheet specification determining unit is configured to determine the shape and dimensions of a sheet by acquiring the body surface information of the individual user; and determining the shape and the dimension of the sheet for the individual user based on the acquired body surface information by:

prompting a user to select a sheet shape; and prompting the user to determine an application position of the sheet and a size of the sheet, and wherein the shape and the dimensions of the sheet suited to the user are determined based on the body surface information, the sheet shape selected by the user, and the information regarding the application position of the sheet and the size of the sheet determined by the user.

9. The system according to claim 8, wherein the sheet forming unit forms the sheet by moving the discharge nozzle along a trajectory based on the information regarding the shape and the dimensions of the sheet while discharging the raw material from the discharge nozzle.

10. The system according to claim 8, wherein the sheet forming unit forms the sheet by discharging the raw material while applying a voltage.

11. The system according to claim 8, wherein:

the sheet specification determining unit is connected to an information terminal or a body surface information acquiring apparatus via a network, the sheet specification determining unit comprises a communication unit, a sheet information generating unit, and an input information analyzing unit, the communication unit is configured to receive the body surface information of the individual user from each of the information terminal and the body surface information acquiring apparatus, and transmit information generated or computed by the sheet information generating unit or the input information analyzing unit to at least one selected from the group consisting of the information terminal, the body surface information acquiring apparatus, and the sheet forming unit, the sheet information generating unit is configured to transmit, based on the information received by the communication unit, information regarding a selection operation screen for prompting the user to select a sheet shape, and information regarding an adjustment operation screen for prompting the user to adjust an application position of the sheet and a size of the sheet to the information terminal or the body surface information acquiring apparatus via the communication unit, and the input information analyzing unit is configured to compute a shape and dimensions of the sheet based on the body surface information of the user, the sheet shape selected by the user, and information regarding the application position and the size of the sheet determined by the user.

12. The system according to claim 8, wherein the body surface information includes information regarding at least one selected from the group consisting of a body part to which the sheet is to be applied, and a skin color, skin unevenness, skin moisture content, and skin viscoelasticity of the body part.

13. The system according to claim 8, further comprising a storage unit that stores the body surface information.

14. The system according to claim 8, wherein the sheet comprises a sheet layer made of the raw material, and the sheet layer has a maximum thickness of 5.1 μm or more and 500 μm or less.

15. The system according to claim 8, wherein the sheet is made of fibers formed from the raw material, and the fibers have a fiber diameter of 0.1 μm or more and 6.0 μm or less.

16. An apparatus for producing a sheet configured to be applied to a body surface of an individual user, the apparatus comprising:

a sheet specification determining unit configured to determine a shape and dimensions of a sheet for an individual user based on body surface information of the individual user;

a sheet forming unit that includes a discharge nozzle configured to form the sheet by discharging a raw material of the sheet through the discharge nozzle to form a sheet having the shape and the dimensions of the sheet for the individual user; and a sheet formation instructing unit configured to generate control instruction information for controlling the discharge nozzle of the sheet forming unit, wherein the sheet specification determining unit is configured to determine the shape and dimensions of a sheet by acquiring the body surface information of the individual user; and determining the shape and the dimension of the sheet for the individual user based on the acquired body surface information by:

prompting a user to select a sheet shape; and prompting the user to determine an application position of the sheet and a size of the sheet, and wherein the shape and the dimensions of the sheet suited to the user are determined based on the body surface information, the sheet shape selected by the user, and the information regarding the application position of the sheet and the size of the sheet determined by the user.

* * * * *